United States Patent

Sato et al.

[11] Patent Number: 5,672,712
[45] Date of Patent: Sep. 30, 1997

[54] THIAZOLINE DERIVATIVES

[75] Inventors: Masakazu Sato; Akira Manaka; Keiko Takahashi; Yutaka Kawashima; Katsuo Hatayama, all of Tokyo, Japan

[73] Assignee: Taisho Pharmaceutical Co., Ltd., Tokyo, Japan

[21] Appl. No.: 750,521

[22] PCT Filed: Jun. 12, 1995

[86] PCT No.: PCT/JP95/01169

§ 371 Date: Dec. 12, 1996

§ 102(e) Date: Dec. 12, 1996

[87] PCT Pub. No.: WO95/34543

PCT Pub. Date: Dec. 21, 1995

[30] Foreign Application Priority Data

Jun. 13, 1994 [JP] Japan .................. 6-130149
Aug. 29, 1994 [JP] Japan .................. 6-203586

[51] Int. Cl.$^6$ .................................... C07D 277/56
[52] U.S. Cl. .................................... 548/195
[58] Field of Search .................................... 548/195

[56] References Cited

U.S. PATENT DOCUMENTS 5,478,945 12/1995 Sato .................. 548/195
5,510,478 4/1996 Sabb .................. 540/585

FOREIGN PATENT DOCUMENTS

WO 94/02472 2/1994 WIPO .................. C07D 277/48

*Primary Examiner*—Robert Gerstl
*Attorney, Agent, or Firm*—Sughrue, Mion, Zinn, Macpeak and Seas

[57] ABSTRACT

Object: To provide compounds useful as inhibitors of blood platelet aggregation for intravenous administration.

Constitution: A thiazoline derivative represented by the formula:

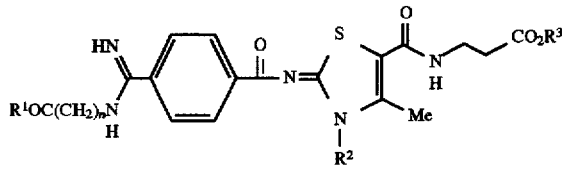

[wherein $R^1$ is a hydroxyl group, an alkoxy group, a cycloalkoxy group or a group represented by the formula: $R^4NH$— (wherein $R^4$ is a cycloalkyl group), $R^2$ is an alkyl group, a cycloalkyl group or a phenylalkyl group, $R^3$ is a hydrogen atom or an alkyl group, and n is an integer of 2 to 9] or a salt thereof.

5 Claims, No Drawings

THIAZOLINE DERIVATIVES

This application is a 371 of PCT/JP95/01169 filed Jun. 12, 1995.

TECHNICAL FIELD

The present invention relates to novel thiazoline derivatives having an inhibitory action of blood platelet aggregation.

BACKGROUND ART

Blood platelet aggregation is considered to occur by the appearance of the binding site to the fibrinogen on the blood platelet membrane glycoprotein GPIIb/IIIa complex caused by stimulation of various blood platelet aggregation-inducing substances. Accordingly, the compounds having an antagonism to fibrinogen receptors have a possibility to show an inhibitory action of blood platelet aggregation.

Compounds disclosed in WO 94/02472 are thiazoline derivatives having an antagonism of fibrinogen receptors, thereby having an inhibitory action of blood platelet aggregation.

However, the compounds disclosed in WO 94/02472 are lowly water-soluble and have a problem of stability in an aqueous solution. Therefore, when administered in the form of an injection solution, these compounds are insufficient for utility as medicines.

An object of the present invention is to provide compounds having an excellent inhibitory action of blood platelet aggregation and good solubility in water, i.e. compounds practicable as an inhibitor of blood platelet aggregation for intravenous administration.

DISCLOSURE OF THE INVENTION

As a result of extensive researches, the present inventors have found that certain thiazoline derivatives achieve the above-mentioned object, and thereby the present invention has been accomplished.

The present invention is a thiazoline derivative represented by Formula:

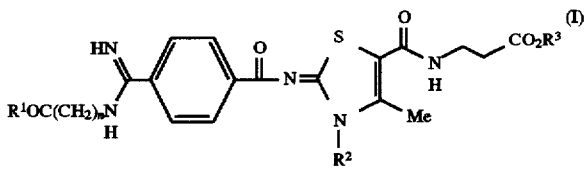

[wherein $R^1$ is a hydroxyl group, an alkoxy group having 1 to 6 carbon atoms, a cycloalkoxy group having 3 to 6 carbon atoms or a group represented by the formula:

(wherein $R^4$ is a cycloalkyl group having 3 to 6 carbon atoms or a phenyl group), $R^2$ is an alkyl group having 1 to 14 carbon atoms, a cycloalkyl group having 3 to 6 carbon atoms or a phenylalkyl group having 7 to 10 carbon atoms, $R^3$ is a hydrogen atom or an alkyl group having 1 to 6 carbon atoms, and n is an integer of 2 to 9] or a pharmaceutically acceptable salt thereof.

In the present invention, the alkyl group as used by itself or as a part of certain group refers to a straight or branched alkyl group, i.e., examples of the alkyl group having 1 to 6 carbon atoms are a methyl group, an ethyl group, a propyl group, an isopropyl group, a butyl group, an isobutyl group, a tert-butyl group, a pentyl group, an isopentyl group and a hexyl group, and examples of the alkyl group having 1 to 14 carbon atoms are, besides the group given above, a 2-methylhexyl group, a 3-methylhexyl group, a heptyl group, an octyl group, a decyl group and a tetradecyl group. In addition, the cycloalkyl group having 3 to 6 carbon atoms refers to a cyclopropyl group, a cyclobutyl group, a cyclopentyl group and a cyclohexyl group. Examples of the phenylalkyl group having 7 to 10 carbon atoms are a benzyl group, a phenethyl group and a phenylpropyl group.

The pharmaceutically acceptable salt of the compound of Formula (I) refers to, for example, salts with an alkali metal, an alkali earth metal, ammonia, an alkylamine, a mineral acid, a carboxylic acid or a sulfonic acid, and more especially sodium salt, potassium salt, calcium salt, ammonium salt, aluminium salt, triethylammonium salt, hydrochloride, hydrobromide, hydroiodide, sulfate, nitrate, phosphate, monomethylsulfate, acetate, propionate, butyrate, succinate, tartrate, citrate, tannate, malate, caproate, valerate, fumarate, maleate, methanesulfonate, tosylate or trifluoroacetate.

Preferred compounds of the present invention are those wherein $R^3$ is a hydrogen atom, especially those wherein $R^1$ is a hydroxyl group and $R^3$ is a hydrogen atom, and more especially those wherein $R^1$ is a hydroxyl group, $R^3$ is a hydrogen atom and $R^2$ is a methyl group.

The most preferred compounds of the present invention are N-(2-carboxyethyl)-2-{4-[N-(3-carboxypropyl)amidino]benzoylimino}-3,4-dimethyl-3H-thiazoline-5-carboxamide and N-(2-carboxyethyl)-2-{4-[N-(2-carboxyethyl)amidino]benzoylimino}-3,4-dimethyl-3H-thiazoline-5-carboxamide.

The compounds of the present invention can be prepared by the following methods.

For the preparation of the compounds of the present invention, first, a compound represented by the following Formula (a):

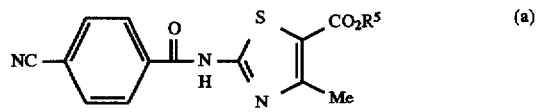

(wherein $R^5$ is an alkyl group having 1 to 6 carbon atoms), which can be obtained by reacting 4-cyanobenzoyl chloride with a 4-methyl-2-aminothiazole-5-carboxylate, is reacted with an alkylating agent such as, for example, a halide represented by the formula:

(wherein X is a halogen atom and $R^2$ is as defined above), a compound represented by the formula:

(wherein $R^2$ is as defined above) or a sulfonate (e.g. methyl methanesulfonate) represented by the formula:

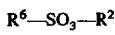

(wherein $R^6$ is an alkyl group or an aryl group, and $R^2$ is as defined above) in the presence of a base to give a compound represented by Formula (b):

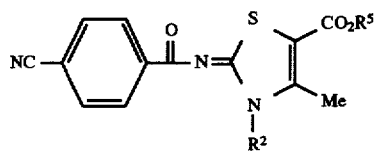

(b)

(wherein $R^2$ and $R^5$ are as defined above).

Alternatively, the compound of Formula (b) may be also prepared by the following method.

A compound represented by the following Formula (c):

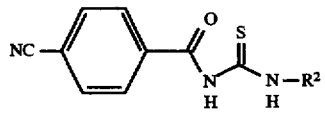

(c)

(wherein $R^2$ is as defined above) which can be prepared, for example, by the method described in Org. Synth. Coll., vol. 3, page 735, is reacted with a compound represented by the formula:

$$CH_3COCH(X)CO_2R^5$$

(wherein X is a halogen atom and $R^5$ is as defined above) in the presence or absence of a base in a solvent or without solvent under heating to give a compound of Formula (b).

Next, the ester moiety of the compound of Formula (b) is hydrolyzed according to a conventional method to lead to a compound represented by Formula (d):

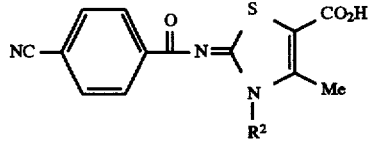

(d)

(wherein $R^2$ is as defined above) or a salt thereof, and the resulting compound is amidated using a compound represented by the formula:

$$H_2N\text{—}(CH_2)_2\text{—}CO_2R^7$$

(wherein $R^7$ is $R^3$ other than a hydrogen atom) or a salt thereof according to a conventional method for formation of amide linkage to give a compound represented by Formula (e):

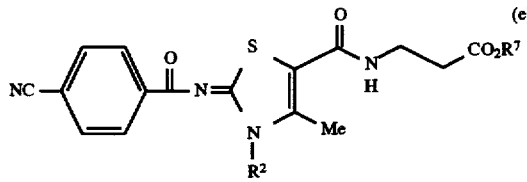

(e)

(wherein $R^2$ and $R^7$ are as defined above). The compound of Formula (e) is subjected, for example, to a reaction with hydrogen sulfide by using a base as a catalyst, or a reaction with $NaBH_2S_3$ to lead to a compound represented by Formula (f):

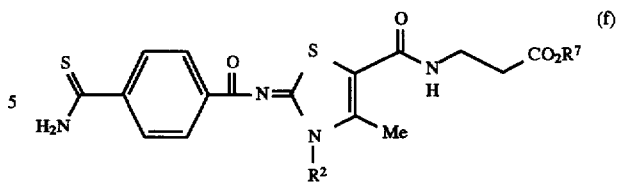

(f)

(wherein $R^2$ and $R^7$ are as defined above), which is then treated with a lower alkyl halide represented by the formula:

$$R^8\text{—}X$$

(wherein $R^8$ is an alkyl group having 1 to 6 carbon atoms, and X is a halogen atom) or a compound of the formula:

$$R^8{}_2\text{—}SO_4$$

(wherein $R^8$ is as defined above) to lead to a compound represented by Formula (g):

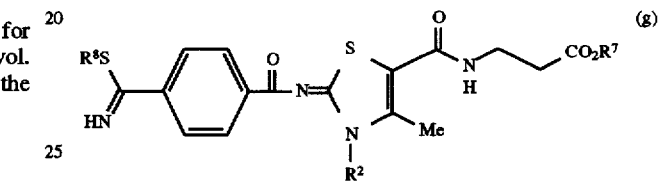

(g)

(wherein $R^2$, $R^7$ and $R^8$ are as defined above) or a salt thereof. This compound is treated with a compound represented by Formula (h):

$$R^1OC(CH_2)_nNH_2$$ (h)

(wherein $R^1$ and n are as defined above) or a salt thereof in the presence or absence of an acid or a base to lead to a compound of the present invention wherein $R^3$ is an alkyl group having 1 to 6 carbon atoms.

The compound of the present invention wherein $R^3$ is a hydrogen atom or a salt thereof can be also prepared by hydrolysis of the ester moiety of the compound of the present invention wherein $R^3$ is an alkyl group having 1 to 6 carbon atoms. The hydrolysis of the ester to be used is an ordinary method such as treatments with an alkali, a mineral acid or an organic acid. The compounds of the present invention wherein $R^3$ is an alkyl group having 1 to 6 carbon atoms can be also converted each other by transesterification using an acid as a catalyst.

Examples of the base to be used in the above-mentioned reaction are an alkali metal salt (e.g. sodium carbonate, potassium carbonate, sodium bicarbonate, potassium bicarbonate, sodium hydroxide, potassium hydroxide, dimsyl sodium, sodium hydride, sodium amide or potassium tert-butyl), an amine (e.g. triethylamine, diisopropylethylamine or pyridine), sodium acetate and potassium acetate; examples of the mineral acid are hydrochloric acid, hydrobromic acid, hydroiodic acid, nitric acid and sulfuric acid; and examples of the organic acid are acetic acid, methanesulfonic acid and p-toluenesulfonic acid.

Examples of the reaction solvent to be used are reaction-inert solvents such as water, an alcohol (e.g. methanol, ethanol, isopropyl alcohol or tert-butyl alcohol), an ether (e.g. dioxane or tetrahydrofuran), dimethylformamide, dimethyl sulfoxide, pyridine, methylene chloride, chloroform, acetone and acetic acid.

INDUSTRIAL UTILIZABILITY

The thus-obtained compounds of Formula (I) inhibit the binding of various adhesive proteins such as fibrinogen, fibronectin and von Willebrand factor against fibrinogen receptor (GpIIb/IIIa) on blood platelet, and have the inhibitory action of the aggregation and adhesion of blood platelet.

Accordingly, the compounds of the present invention can be used as preventive and therapeutic agents of ischemic diseases (e.g. thrombosis, cerebral infarction or myocardial infarction) and arteriosclerosis diseases.

For the purposes, the compounds of Formula (I) can be mixed with, for example, conventional fillers, pH modulators or solubilizers, and prepared in the form of injection solutions by conventional formulation techniques.

The dose of the compound of Formula (I) for adult patients is 0.01 to 100 mg per day, which can be given in a single dose or in several divided doses. This dose can be increased or decreased depending on the kind of the diseases and the age, body weight and condition of the patient.

Fibrinogen receptor antagonism of the compounds of Formula (I) is illustrated by the following experiments.

Experiment 1 [Human Blood Platelet Fibrinogen Binding Test]

The test was carried out referring to the methods of G. A. Marguerie (J. Biol. Chem., vol. 254, pages. 5357–5363, 1979) and N. S. Nicholson (Thromb. Res., vol. 50, pages 567–578, 1991).

Citrated blood (the volume ratio of 3.13% sodium citrate solution and blood is 1:9) was collected from the cubital vein of a healthy human who had not received any drugs known to affect the function of blood platelet within 2 weeks prior to starting the test, and centrifuged at 120× g at room temperature for 15 minutes to give platelet rich plasma (PRP) as a supernatant.

To the above PRP was added one fifth volume of an ACD solution (citric acid/sodium citrate/dextrose), followed by centrifugation at 1200× g for 15 minutes. The precipitate was suspended in a Tyrode's solution (20% fetal bovine serum, 2 mM $Mg^{2+}$), followed by gel filtration using Sepharose 2B column to give a fibrinogen-free blood platelet suspension ($1\times10^9$/ml). The binding test was carried out by using the fibrinogen-free blood platelet suspension, the solutions of the compounds of Formula (I) in dimethyl sulfoxide which were each adjusted to the desired concentration by diluting with a physiological saline solution as test drugs, ADP (final concentration: 10 µM) and $^{125}$I labeled human fibrinogen, and then the binding inhibitory rate of the test drug was calculated.

N-(2-Carboxyethyl)-2-(4-amidinobenzoylimino)-3,4-dimethyl-3H-thiazoline-5-carboxamide hydrobromide (described in WO 94/02472; referred to as "Comparative drug" in the following experiments) was used as a comparative drug. The drug solution was prepared in the same manner as described above, and tested as described above.

The results are shown in Table 1 in which the compound numbers are the same as defined in the following examples and are also used in the following experiments.

TABLE 1

| Test drug | $IC_{50}$ value (nM) |
| --- | --- |
| Compound 8 | 25.6 |
| Compound 9 | 16.5 |
| Compound 11 | 8.2 |
| Compound 12 | 4.7 |
| Compound 17 | 12.6 |

TABLE 1-continued

| Test drug | $IC_{50}$ value (nM) |
| --- | --- |
| Compound 49 | 7.2 |
| Compound 51 | 8.6 |
| Compound 56 | 11.1 |
| Comparative drug | 5.0 |

Experiment 2 [Human in vitro Blood Platelet Aggregation Inhibition Test]

Citrated blood (the volume ratio of 3.13% sodium citrate solution and blood is 1:9) was collected from the cubital vein of a healthy human who had not received any drugs known to affect the function of blood platelet within 2 weeks prior to starting the test, and centrifuged at 120× g at room temperature for 15 minutes to give platelet rich plasma (PRP) as a supernatant. The remaining precipitate was further centrifuged at 1500× g for 10 minutes to give platelet poor plasma (PPP) as a supernatant. The blood platelet counts of PRP were adjusted to 50–60×$10^4$/µl by diluting with PPP.

Blood platelet aggregation was monitored according to the method of Born G. V. R., [Nature, vol. 194, page 927 (1962)] using adenosine diphosphate (produced by Sigma Co.; hereinafter referred to as "ADP") as an aggregation-inducing substance. That is, a solution of the compound of Formula (I) as a test drug in dimethyl sulfoxide was adjusted to the desired concentration with a physiological saline solution. 25 µl of the solution was added to 250 µl of PRP and incubated at 37° C. for 3 minutes, and 25 µl of ADP (final concentration: 7 µM) was added thereto. The mixture was measured for 5 minutes by using a blood platelet aggregation ability measurement apparatus (Aggricoda TM•PA-3210; made by Kyoto Daiichi Kagaku Co.) to give the maximum aggregation, and the concentration of the test drug to bring 50% inhibition of the maximum aggregation ($IC_{50}$) was calculated.

Results are shown in Table 2.

TABLE 2

| Test drug | $IC_{50}$ value (nM) |
| --- | --- |
| Compound 8 | 39 |
| Comparative drug | 17 |

Experiment 3 [Solubility Test]

Solubility test was carried out referring to the method of S. Miyazaki et al. [Chem. Pharm. Bull., vol. 23, page 1197 (1975)].

9.511 g of disodium hydrogenphosphate weighed accurately was dissolved in 800 ml of water. The solution was adjusted to pH 7.0 by adding sodium dihydrogenphosphate, and the total volume of the solution was made exactly 1000 ml to give a 0.1M phosphate buffer (pH 7). To 1.0 ml of the buffer solution measured exactly was added an excess amount for the solubility limit of the test drug. The suspension was treated by supersonic waves for 5 minutes and stirred on a water bath at 25° C. for 24 hours. After removal of the insoluble substance by using a membrane filter (0.22 µm), the filtrate was appropriately diluted to give a test solution. Separately, 1 mg of the test drug weighed accurately was dissolved in the eluate to make exactly 100 ml to give a standard solution. The test solution and the standard solution were quantified by high performance liquid chromatography method under the following procedure conditions, and the solubility of the test drug was calculated.

The results are shown in Table 3.

Procedure Conditions:

Detection instrument: Ultraviolet spectrophotometer (Detection wave length: 246 nm)

Column: ODS column 4.6φ×150 mm (TSK Gel ODS 80TM)

Column temperature: A definite temperature in the vicinity of 50° C.

Mobile phase: Water:acetonitrile:sodium dodecylsulfate:phosphoric acid=400:600:3:1

Flow rate: 1.0 ml/min.

Injection amount: 10 μl

TABLE 3

| Test drug | Solubility (mg/ml |
| --- | --- |
| Compound 8 | 20 |
| Comparative drug | 0.03 |

Experiment 4 [Stability Test]

Stability test was carried out referring to the method of A. K. Amirjahed et al [J. Pharm. Sci., vol. 66, page 785 (1977)].

20 mg of Compound 8 obtained in the following example and 20 mg of Comparative drug, each weighed accurately, were each dissolved in 0.1N phosphate buffer (a buffer of a suitable amount of 0.1M potassium dihydrogenphosphate mixed with a suitable amount of 0.1M disodium hydrogenphosphate to adjust to pH 7) to make exactly 1000 ml to give standard solutions, respectively. The solution was dispensed into ampules, and they were stored at 80° C. for 4 hours, 8 hours and 24 hours to prepare test solutions.

20 μl of the test solution and 20 μl of the standard solution were each quantified by high performance liquid chromatography method under the following procedure conditions, and the peak areas of Compound 8 and Comparative drug at the storage times were determined, and the remaining rate was calculated by using the following formula, and the results are shown in Table 4.

Detection instrument: Ultraviolet spectrophotometer (Detection wave length: 247 nm)

Column: ODS column 4.6φ×150 mm (TSK Gel ODS 80TM)

Column temperature: A definite temperature in the vicinity of 50° C.

Mobile phase:

[Compound 8] 1 ml of phosphoric acid and 5 g of sodium dodecylsulfate (SDS) are added to 1000 ml of a mixture of water and acetonitrile (65:35).

[Comparative drug] 1 ml of phosphoric acid and 3 g of sodium dodecylsulfate (SDS) are added to 1000 ml of a mixture of water and acetonitrile (60:40).

Flow rate: 1 ml/min.

Formula: Remaining rate (%)=

$$\frac{\text{Peak area at the storage time}}{\text{Peak area of the standard solution}} \times 100$$

TABLE 4

| | Remaining rate (%) of Test drug | |
| --- | --- | --- |
| Storage time | Compound 8 | Comparative drug |
| Immediately after | 100 | 100 |
| After 4 hours | 97.8 | 82.2 |
| After 8 hours | 95.7 | 68.4 |
| After 24 hours | 88.9 | 32.3 |

BEST MODE FOR CARRYING OUT THE INVENTION

The present invention is illustrated in more detail by the following examples. The structures of the compounds obtained in Examples are shown in the following Table 5.

TABLE 5

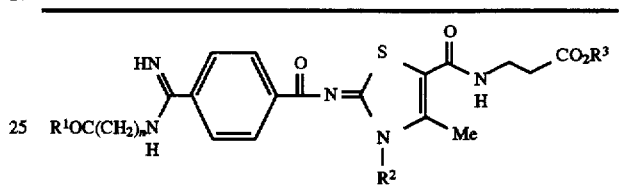

| Compound No. | $R^1$ | n | $R^2$ | $R^3$ | Salt |
| --- | --- | --- | --- | --- | --- |
| 1 | OH | 3 | Me | Me | HI |
| 2 | OH | 2 | Me | Me | HI |
| 3 | OH | 5 | Me | Me | HI |
| 4 | OMe | 3 | Me | Me | MeOSO$_3$H |
| 5 | OMe | 2 | Me | Me | MeOSO$_3$H |
| 6 | O-c.Hex | 3 | Me | Me | MeOSO$_3$H |
| 7 | NH-c.Hex | 3 | Me | Me | MeOSO$_3$H |
| 8 | OH | 3 | Me | H | |
| 9 | OH | 2 | Me | H | |
| 10 | OH | 5 | Me | H | |
| 11 | O-c.Hex | 3 | Me | H | |
| 12 | NH-c.Hex | 3 | Me | H | |
| 13 | O-c.Hex | 3 | i-Pr | Me | MeOSO$_3$H |
| 14 | OMe | 3 | i-Pr | Me | HI |
| 15 | OH | 3 | i-Pr | Me | MeOSO$_3$H |
| 16 | OH | 3 | i-Pr | H | |
| 17 | O-c.Hex | 3 | i-Pr | H | |
| 18 | O-c.Hex | 3 | n-Bu | Me | MeOSO$_3$H |
| 19 | O-c.Hex | 3 | n-Bu | H | |
| 20 | OH | 3 | n-Bu | H | |
| 21 | OH | 3 | C$_6$H$_{13}$ | t-Bu | |
| 22 | OMe | 3 | C$_6$H$_{13}$ | t-Bu | |
| 23 | O-c.Hex | 3 | C$_6$H$_{13}$ | t-Bu | |
| 24 | OH | 3 | C$_6$H$_{13}$ | H | CF$_3$CO$_2$H |
| 25 | OMe | 3 | C$_6$H$_{13}$ | H | CF$_3$CO$_2$H |
| 26 | O-C.Hex | 3 | C$_6$H$_{13}$ | H | CF$_3$CO$_2$H |
| 27 | OH | 3 | H$_{14}$H$_{29}$ | t-Bu | |
| 28 | OMe | 3 | H$_{14}$H$_{29}$ | t-Bu | |
| 29 | O-c.Hex | 3 | H$_{14}$H$_{29}$ | t-Bu | |
| 30 | OH | 3 | H$_{14}$H$_{29}$ | H | CF$_3$CO$_2$H |
| 31 | OMe | 3 | H$_{14}$H$_{29}$ | H | CF$_3$CO$_2$H |
| 32 | O-c.Hex | 3 | H$_{14}$H$_{29}$ | H | CF$_3$CO$_2$H |
| 33 | OMe | 3 | Bn | Me | MeOSO$_3$H |
| 34 | O-c.Hex | 3 | Bn | Me | MeOSO$_3$H |
| 35 | OH | 3 | Bn | H | |
| 36 | O-c.Hex | 3 | Bn | H | |
| 37 | OH | 3 | Ph(CH$_2$)$_2$ | t-Bu | |
| 38 | OMe | 3 | Ph(CH$_2$)$_2$ | t-Bu | |
| 39 | O-c.Hex | 3 | Ph(CH$_2$)$_2$ | t-Bu | |
| 40 | OH | 3 | Ph(CH$_2$)$_2$ | H | CF$_3$CO$_2$H |
| 41 | OMe | 3 | Ph(CH$_2$)$_2$ | H | CF$_3$CO$_2$H |
| 42 | O-c.Hex | 3 | Ph(CH$_2$)$_2$ | H | CF$_3$CO$_2$H |
| 43 | OMe | 3 | c.Pr | Me | |
| 44 | O-c.Hex | 3 | c.Pr | Me | MeOSO$_3$H |
| 45 | NH-c.Hex | 3 | c.Pr | Me | MeOSO$_3$H |
| 46 | NHPh | 5 | c.Pr | Me | MeOSO$_3$H |

TABLE 5-continued

Structure:
HN=C(R¹OC(CH₂)ₙNH-)—C₆H₄—C(O)—N=C(S—)—C(=C(Me)(NR²))—C(O)—NH—CH₂CH₂—CO₂R³

| Compound No. | R¹ | n | R² | R³ | Salt |
|---|---|---|---|---|---|
| 47 | OH | 3 | c.Pr | Me | MeOSO₃H |
| 48 | OH | 3 | c.Pr | H | |
| 49 | O-c.Hex | 3 | c.Pr | H | |
| 50 | NH-c.Hex | 3 | c.Pr | H | |
| 51 | NHPh | 5 | c.Pr | H | |
| 52 | OMe | 3 | c.Bu | Me | |
| 53 | O-c.Hex | 3 | c.Bu | Me | MeOSO₃H |
| 54 | OH | 3 | c.Bu | Me | MeOSO₃H |
| 55 | OH | 3 | c.Bu | H | |
| 56 | O-c.Hex | 3 | c.Bu | H | |
| 57 | OMe | 3 | c.Pn | Me | |
| 58 | O-c.Hex | 3 | c.Pn | Me | MeOSO₃H |
| 59 | OH | 3 | c.Pn | Me | MeOSO₃H |
| 60 | OH | 3 | c.Pn | H | |
| 61 | O-c.Hex | 3 | c.Pn | H | |
| 62 | OH | 2 | c.Hex | Me | HI |
| 63 | OH | 3 | c.Hex | Me | HI |
| 64 | OH | 5 | c.Hex | Me | HI |
| 65 | OH | 2 | c.Hex | H | |
| 66 | OH | 3 | c.Hex | H | |
| 67 | OH | 5 | c.Hex | H | |

In Table 5, "c.Pr" is a cyclopropyl group, "c.Bu" is a cyclobutyl group, "c.Pn" is a cyclopentyl group, "c.Hex" is a cyclohexyl group and "Bn" is a benzyl group.

EXAMPLE 1

(1) Ethyl 2-(4-cyanobenzoylamino)-4-methylthiazole-5-carboxylate (22.07 g) was added to a suspension of 60% oily sodium hydride (3.08 g) in N,N-dimethylformamide (hereinafter referred to as DMF) (300 ml) under ice-cooling, followed by stirring at room temperature for an hour. A solution of methyl iodide (4.8 ml) in DMF (50 ml) was added dropwise to the reaction mixture, followed by further stirring at room temperature for an hour. The reaction mixture was taken up in 3% hydrochloric acid, and the precipitated crystals were collected by filtration, and the resulting crude crystals were recrystallized from a mixture of methylene chloride and methanol to give ethyl 2-(4-cyanobenzoylimino)-3,4-dimethylthiazoline-5-carboxylate (15.97 g).

m.p. 244°~245° C.

(2) 10% Aqueous sodium hydroxide solution (48 ml) was added to a mixture of ethyl 2-(4-cyanobenzoylimino)-3,4-dimethylthiazoline-5-carboxylate (9.88 g), methylene chloride (250 ml) and methanol (250 ml), followed by stirring at room temperature for 17 hours. The reaction mixture was concentrated under reduced pressure, and the precipitated crystals were collected by filtration to give sodium 2-(4-cyanobenzoylimino)-3,4-dimethylthiazoline-5-carboxylate (10.0 g).

¹H-NMR (DMSO-d₆) δ (ppm); 2.66 (3H, s), 3.75 (3H, s), 7.91 (2H, d, J=8Hz), 8.33 (2H, d, J=8Hz).

(3) β-Alanine methyl ester hydrochloride (4.68 g), 1-hydroxybenzotriazole monohydrate (hereinafter referred to as "HOBt.H₂O") (9.34 g) and 1-ethyl-3-{3-(dimethylamino)propyl}carbodiimide hydrochloride (hereinafter referred to as "WSC.HCl") (6.43 g) were successively added to a of suspension of sodium 2-(4-cyanobenzoylimino)-3,4-dimethylthiazoline-5-carboxylate (9.85 g) in DMF with stirring, followed by stirring at room temperature for 14 hours. The reaction mixture was taken up in water, and the precipitated crystals were collected by filtration and recrystallized from a mixture of methylene chloride and hexane to give N-(2-methoxycarbonylethyl)-2-(4-cyanobenzoylimino)-3,4-dimethyl-3H-thiazoline-5-carboxamide (9.9 g).

m.p. 187.5°~189.5° C.

(4) A mixture of N-(2-methoxycarbonylethyl)-2-(4-cyanobenzoylimino)-3,4-dimethyl-3H-thiazoline-5-carboxamide (9.66 g), sodium hydrosulfide (70%, 3.7 g), magnesium chloride hexahydrate (4.7 g) and DMF (175 ml) was stirred at room temperature for an hour. After addition of water (700 ml), the precipitated crystals were collected by filtration, and the resulting crude crystals were washed with 3% hydrochloric acid to give N-(2-methoxycarbonylethyl)-2-(4-thiocarbamoylbenzoylimino)-3,4-dimethyl-3H-thiazoline-5-carboxamide (10.56 g).

m.p. 215.5°~216.5° C.

(5) Methyl iodide (28 ml) was added in 4-portions at 30 minute intervals to a suspension of N-(2-methoxycarbonylethyl)-2-(4-thiocarbamoylbenzoylimino)-3,4-dimethyl-3H-thiazoline-5-carboxamide (6.31 g) in acetone (1600 ml) under heating reflux, followed by stirring for 4 hours. The reaction mixture was concentrated under reduced pressure, and the precipitated crystals were collected by filtration to give N-(2-methoxycarbonylethyl)-2-[4-(methylthioimidoyl)benzoylimino]-3,4-dimethyl-3H-thiazoline-5-carboxamide hydroiodide (7.69 g).

m.p. 203.5°~204° C.

(6) A mixture of N-(2-methoxycarbonylethyl)-2-(4-thiocarbamoylbenzoylimino)-3,4-dimethyl-3H-thiazoline-5-carboxamide obtained in (4) (104 g), DMF (400 ml) and dimethyl sulfate (86.1 ml) was stirred at room temperature for 4 hours. Acetone (1.5 l) was added, and the resulting crystals were collected by filtration and washed with acetone to give N-(2-methoxycarbonylethyl)-2-[4-(methylthioimidoyl)benzoylimino]-3,4-dimethyl-3H-thiazoline-5-carboxamide methylsulfate (126.45 g).

m.p. 164°~167° C.

(7) N-(2-Methoxycarbonylethyl)-2-[4-(methylthioimidoyl)benzoylimino]-3,4-dimethylthiazoline-5-carboxamide hydroiodide (2.0 g) was added to a mixture of 4-aminobutyric acid (0.37 g), acetic acid (0.2 ml) and methanol (20 ml) under heating reflux, and the mixture was further heated under reflux for an hour. The reaction mixture was concentrated, and the precipitated crystals were collected by filtration to give N-(2-methoxycarbonylethyl)-2-{4-[N-(3-carboxypropyl)amidino]benzoylimino}-3,4-dimethyl-3H-thiazoline-5-carboxamide hydroiodide (Compound 1).

m.p. 204°~210° C.

Following the reaction procedure similar to that of Example 1, the following compounds were obtained.

N-(2-Methoxycarbonylethyl)-2-{4-[N-(2-carboxyethyl)amidino]benzoylimino}-3,4-dimethyl-3H-thiazoline-5-carboxamide hydroiodide (Compound 2)

m.p. 175°~177° C.

N-(2-Methoxycarbonylethyl)-2-{4-[N-(5-carboxypentyl)amidino]benzoylimino}-3,4-dimethyl-3H-thiazoline-5-carboxamide hydroiodide (Compound 3)

m.p. 210°~213° C.

EXAMPLE 2

N-(2-Methoxycarbonylethyl)-2-[4-(methylthioimidoyl)benzoylimino]-3,4-dimethylthiazoline-5-carboxamide methylsulfate (10.0 g) obtained in Example 1(6) was added to a mixture of methyl 4-aminobutyrate hydrochloride (2.81 g), sodium acetate (1.5 g) and methanol (100 ml) under heating reflux, and the reaction mixture was further heated under reflux for an hour. The reaction mixture was concentrated and the resulting crystals were collected by filtration to give N-(2-methoxycarbonylethyl)-2-{4-[N-(3-methoxycarbonylpropyl)amidino]benzoylimino}-3,4-dimethyl-3H-thiazoline-5-carboxamide methylsulfate (Compound 4).

m.p. 209.5°~210° C.

Following the reaction procedure similar to that of Example 2, the following compound was obtained.

N-(2-Methoxycarbonylethyl)-2-{4-[N-(2-methoxycarbonylethyl)amidino]benzoylimino}-3,4-dimethyl-3H-thiazoline-5-carboxamide methylsulfate (Compound 5).

m.p. 196°~198.5° C.

EXAMPLE 3

N-(2-Methoxycarbonylethyl)-2-[4-(methylthioimidoyl)benzoylimino]-3,4-dimethyl-3H-thiazoline-5-carboxamide methylsulfate (2.0 g) obtained in Example 1(6) was added to a mixture of cyclohexyl 4-aminobutyrate methanesulfonate (1.63 g), sodium acetate (0.45 g) and methanol (20 ml) under heating reflux, and the reaction mixture was further heated under reflux for an hour. To the reaction mixture was added acetone (40 ml), and the precipitated crystals were collected by filtration to give N-(2-methoxycarbonylethyl)-2-{4-[N-(3-cyclohexyloxycarbonylpropyl)amidino]benzoylimino}-3,4-dimethyl-3H-thiazoline-5-carboxamide methylsulfate (Compound 6).

m.p. 217°~217.5° C.

EXAMPLE 4

Following the procedure similar to that of Example 3 using 4-amino-N-cyclohexylbutyramide hydrochloride in place of cyclohexyl 4-aminobutyrate methanesulfonate, N-(2-methoxycarbonylethyl)-2-{4-[N-(3-cyclohexylaminocarbonylpropyl)amidino]benzoylimino}-3,4-dimethyl-3H-thiazoline-5-carboxamide methylsulfate (Compound 7) was obtained.

m.p. 228°~228.5° C.

EXAMPLE 5

10% Aqueous sodium hydroxide solution (210 ml) was added to a mixture of Compound 4 (64.5 g), methanol (323 ml) and 2-propanol (323 ml), followed by stirring at room temperature for an hour. The reaction solution was poured into 50% acetic acid (645 ml), and after ice-cooling, the precipitated crystals were collected by filtration to give N-(2-carboxyethyl)-2-{4-[N-(3-carboxypropyl)amidino]benzoylimino}-3,4-dimethyl-3H-thiazoline-5-carboxamide (Compound 8).

m.p. 249.5°~250° C.

EXAMPLE 6

A mixture of Compound 2 (0.25 g), 10% aqueous sodium hydroxide solution (0.84 ml) and methanol (5 ml) was stirred at room temperature for an hour, followed by evaporation under reduced pressure. The residue was dissolved in water and acidified with 3% aqueous hydrochloric acid solution, and the precipitated crystals were collected by filtration to give N-(2-carboxyethyl)-2-{4-[N-(2-carboxyethyl)amidino]-benzoylimino}-3,4-dimethyl-3H-thiazoline-5-carboxamide (Compound 9).

m.p. 215°~218° C. (decomposed)

Following the reaction procedure similar to that of Example 6, the following compound was obtained.

N-(2-Carboxyethyl)-2-{4-[N-(5-carboxypentyl)amidino]benzoylimino}-3,4-dimethyl-3H-thiazoline-5 -carboxamide (Compound 10).

m.p. 230°~231.5° C.

EXAMPLE 7

A mixture of Compound 6 (1.0 g), 10% aqueous sodium hydroxide solution (1.2 ml) and 2-propanol (10 ml) was stirred under ice-cooling for an hour. To the reaction mixture were added 10% aqueous sodium dihydrogen phosphate solution and water, and the precipitated crystals were collected by filtration to give N-(2-carboxyethyl)-2-{4-[N-(3-cyclohexyloxycarbonylpropyl)amidino]benzoylimino}-3,4-dimethyl-3H-thiazoline-5-carboxamide (Compound 11).

m.p. 203.5°~204° C.

EXAMPLE 8

A mixture of Compound 7 (0.3 g), 10% sodium hydroxide solution (0.37 ml) and 2-propanol (3 ml) was stirred at room temperature for 30 minutes. To the reaction mixture was added acetic acid, and the precipitated crystals were collected by filtration to give N-(2-carboxyethyl)-2-{4-[N-(3-cyclohexylaminocarbonylpropyl)amidino]benzoylimino}-3,4-dimethyl-3H-thiazoline-5-carboxamide (Compound 12).

m.p. 217.5°~218° C.

EXAMPLE 9

(1) 4-Cyanobenzoyl chloride (10 g) was added in portions to a solution of ammonium thiocyanate (4.6 g) in acetone (100 ml) at room temperature, followed by heating under reflux for 10 minutes. The reaction mixture was ice-cooled, and after removal of the insoluble substance by filtration, the filtrate was evaporated under reduced pressure to give 4-cyanobenzoyl isothiocyanate (11.2 g).

m.p. 87.5°~88.5° C.

(2) Isopropylamine (5.6 ml) was added dropwise to a mixture of 4-cyanobenzoyl isothiocyanate (11 g) and toluene (100 ml) at 60° C., and the insoluble substance in the reaction solution was filtered off. After allowing to stand for cooling, the precipitated crystals were recrystallized from toluene to give 1-(4-cyanobenzoyl)-3-isopropylthiourea (12.35 g) as pale yellow prisms.

m.p. 156°~157° C.

(3) A mixture of 1-(4-cyanobenzoyl)-3-isopropylthiourea (37 g), ethyl 2-chloroacetoacetate (59 g) and toluene (500 ml) was heated under reflux with removing the water generated in the reaction for 3 hours. The reaction mixture was allowed to stand for cooling, and then the precipitated crystals were collected by filtration and recrystallized from toluene to give ethyl 2-(4-cyanobenzoylimino)-3-isopropyl-4-methyl-3H-thiazoline-5-carboxylate (45 g) as a pale yellow powder.

m.p. 207.5°~209° C.

(4) A mixture of ethyl 2-(4-cyanobenzoylimino)-3-isopropyl-4-methyl-3H-thiazoline-5-carboxylate (45.0 g), 10% aqueous sodium hydroxide solution (55.4 ml), dimethyl sulfoxide (450 ml) and methylene chloride (450 ml) was stirred at room temperature for 2.5 hours. Methylene chloride and conc. hydrochloric acid were added to the reaction mixture, and then the methylene chloride was evaporated. After addition of water, the precipitated crystals were collected by filtration to give 2-(4-cyanobenzoylimino)-3-isopropyl-4-methyl-3H-thiazoline-5-carboxylic acid (42.17 g).

m.p. 261°~264° C. (decomposed)

(5) A mixture of 2-(4-cyanobenzoylimino)-3-isopropyl-4-methyl-3H-thiazoline-5-carboxylic acid (10.0 g), 1,3-dimethyl-2-chloroimidazolium chloride (hereinafter referred to as "DMC") (8.22 g) and β-alanine methyl ester hydrochloride (6.79 g), triethylamine (20.32 ml) and DMF (200 ml) was stirred at room temperature for 14 hours. The reaction solution was poured into water (800 ml), and the precipitated crystals were collected by filtration to give N-(2-methoxycarbonylethyl)-2-(4-cyanobenzoylimino)-3-isopropyl-4-methyl-3H-thiazoline-5-carboxamide (11.67 g).

m.p. 139.5°~140.5° C.

(6) A mixture of N-(2-methoxycarbonylethyl)-2-(4-cyanobenzoylimino)-3-isopropyl-4-methyl-3H-thiazoline-5-carboxamide (11.0 g), sodium hydrosulfide (70%, 4.25 g), magnesium chloride hexahydrate (5.40 g) and DMF (200 ml) was stirred at room temperature for an hour. After addition of water (800 ml), the precipitated crystals were collected by filtration, and the resulting crude crystals were washed with 3% hydrochloric acid to give N-(2-methoxycarbonylethyl)-2-(4-thiocarbamoylbenzoylimino)-3-isopropyl-4-methyl-3H-thiazoline-5-carboxamide (11.34 g).

m.p. 186°~187° C.

(7) A mixture of N-(2-methoxycarbonylethyl)-2-(4-thiocarbamoylbenzoylimino)-3-isopropyl-4-methyl-3H-thiazoline-5-carboxamide (11.0 g), DMF (35 ml) and dimethyl sulfate (10.5 ml) was stirred at room temperature for 2.5 hours. Acetone (100 ml) and hexane (100 ml) were added to the reaction mixture, and the precipitated crystals were collected by filtration to give N-(2-methoxycarbonylethyl)-2-[4-(methylthioimidoyl)benzoylimino]-3-isopropyl-4-methyl-3H-thiazoline-5-carboxamide methylsulfate (12.7 g).

m.p. 158°~162° C.

(8) N-(2-Methoxycarbonylethyl)-2-[4-(methylthioimidoyl)benzoylimino]-3-isopropyl-4-methyl-3H-thiazoline-5-carboxamide methylsulfate (3.0 g) was added to a mixture of cyclohexyl 4-aminobutyrate methanesulfonate (2.47 g), sodium acetate (529 mg) and methanol (30 ml) under heating reflux, and the reaction mixture was further heated under reflux for an hour. After evaporation of the methanol under reduced pressure, the residue was dissolved in methylene chloride and washed with water. After evaporation of the solvent, acetone and toluene were added to the residue, and the solvent was removed by decantation, followed by drying to give N-(2-methoxycarbonylethyl)-2-{4-[N-(3-cyclohexyloxycarbonylpropyl)amidino]benzoylimino}-3-isopropyl-4-methyl-3H-thiazoline-5-carboxamide methylsulfate (Compound 13).

m.p. 88°~90° C.

EXAMPLE 10

Following the reaction procedures similar to those of Examples 1(5) and 9(8) using the compound obtained in Example 9(6), N-(2-methoxycarbonylethyl)-2-{4-[N-(3-methoxycarbonylpropyl)amidino]benzoylimino}-3-isopropyl-4-methyl-3H-thiazoline-5-carboxamide hydroiodide (Compound 14) was obtained.

m.p. 96°~98° C.

EXAMPLE 11

N-(2-Methoxycarbonylethyl)-2-[4-methylthioimidoyl)benzoylimino]-3-isopropyl-4-methyl-3H-thiazoline-5-carboxamide methylsulfate (1.0 g) obtained in Example 9(7) was added to a mixture of 4-aminobutyric acid (190 mg) and methanol (10 ml) under heating reflux, and the reaction mixture was further heated under reflux for an hour. After evaporation of the methanol under reduced pressure, methanol, acetone and isopropyl ether were added to the residue. The solvent was removed by decantation, followed by drying to give N-(2-methoxycarbonylethyl)-2-{4-[N-(3-carboxypropyl)amidino]benzoylimino}-3-isopropyl-4-methyl-3H-thiazoline-5-carboxamide methylsulfate (Compound 15).

m.p. 73°~75° C.

EXAMPLE 12

A mixture of Compound 14 (1.0 g), 10% aqueous sodium hydroxide solution (2.4 ml) and methanol (10 ml) was stirred at room temperature for an hour. To the reaction solution were added acetic acid and water, and the precipitated crystals were collected by filtration to give N-(2-carboxyethyl)-2-{4-[N-(3-carboxypropyl)amidino]benzoylimino}-3-isopropyl-4-methyl-3H-thiazoline-5-carboxamide (Compound 16).

m.p. 160°~162° C.

EXAMPLE 13

Following the procedure similar to that of Example 7 using Compound 13, N-(2-carboxyethyl)-2-{4-[N-(3-cyclohexyloxycarbonylpropyl)amidino]benzoylimino}-3-isopropyl-4-methyl-3H-thiazoline-5-carboxamide (Compound 17) was obtained.

m.p. 170°~174° C.

EXAMPLE 14

(1) 4-Cyanobenzoyl isothiocyanate (8 g) obtained in Example 9(1) was suspended in toluene (50 ml), and n-butylamine (4.2 ml) was added thereto, followed by stirring for 30 minutes. After addition of ethyl 2-chloroacetoacetate (14 ml), the mixture was stirred under heating reflux with removing the water generated in the reaction for 30 minutes. After cooling to room temperature, the precipitated crystals were collected by filtration to give ethyl 3-n-butyl-2-(4-cyanobenzoylimino)-4-methyl-3H-thiazoline-5-carboxylate (8.7 g).

m.p. 186°~187° C.

(2) A mixture of ethyl 3-n-butyl-2-(4-cyanobenzoylimino)-4-methyl-3H-thiazoline-5-carboxylate (8.4 g), 10% aqueous sodium hydroxide solution (36 ml), acetone (100 ml) and methanol (50 ml) was stirred under heating reflux for 6 hours. After cooling to room temperature, 3% hydrochloric acid (100 ml) was added, and the precipitated crystals were collected by filtration to give 3-n-butyl-2-(4-cyanobenzoylimino)-4-methyl-3H-thiazoline-5-carboxylic acid (8.0 g).

A mixture of 3-n-butyl-2-(4-cyanobenzoylimino)-4-methyl-3H-thiazoline-5-carboxylic acid (8 g), WSC.HCl (4.9 g), HOBt.H$_2$O (3.9 g), β-alanine methyl ester hydrochloride (3.6 g), triethylamine (3.6 ml) and DMF (100 ml) was stirred at room temperature for 24 hours. Water (1.2 l) was added to the reaction mixture, and after extraction with methylene chloride, the organic layer was washed with a saturated aqueous sodium bicarbonate solution and a saturated aqueous sodium chloride solution and dried over magnesium sulfate. After concentration under reduced pressure, the precipitated crude crystals were recrystallized from methanol to give N-(2-methoxycarbonylethyl)-3-n-butyl-2-(4-cyanobenzoylimino)-4-methyl-3H-thiazoline-5-carboxamide (8.2 g).

m.p. 155.5°~157.5° C.

(3) A mixture of N-(2-methoxycarbonylethyl)-3-n-butyl-2-(4-cyanobenzoylimino)-4-methyl-3H-thiazoline-5-carboxamide (8.1 g), sodium hydrosulfide (70%, 3.0 g), magnesium chloride hexahydrate (3.84 g) and DMF (80 ml) was stirred at room temperature overnight. After addition of water (300 ml), the precipitated crystals were collected by filtration, and the resulting crude crystals were washed with 3% hydrochloric acid to give N-(2-methoxycarbonylethyl)-2-(4-thiocarbamoylbenzoylimino)-3-n-butyl-4-methyl-3H-thiazoline-5-carboxamide (8.8 g).

m.p. 177°~179.5° C.

(4) N-(2-Methoxycarbonylethyl)-2-(4-thiocarbamoylbenzoylimino)-3-n-butyl-4-methyl-3H-thiazoline-5-carboxamide (8.8 g) was suspended in DMF (50 ml), and then dimethyl sulfate (5.4 ml) was added thereto, followed by stirring at 60° C. for 5 hours. After cooling to room temperature, acetone (200 ml) and hexane (150 ml) were added to the reaction mixture, and the precipitated crystals were collected by filtration to give N-(2-methoxycarbonylethyl)-2-[4-(methylthioimidoyl)benzoylimino]-3-n-butyl-4-methyl-3H-thiazoline-5-carboxamide methylsulfate (12.1 g).

m.p. 110°~113° C.

(5) Following the procedure similar to that of Example 3 using N-(2-methoxycarbonylethyl)-2-[4-(methylthioimidoyl)benzoylimino]-3-n-butyl-4-methyl-3H-thiazoline-5-carboxamide methylsulfate (1 g), N-(2-methoxycarbonylethyl)-2-{4-[N-(3-cyclohexyloxycarbonylpropyl)amidino]benzoylimino}-3-n-butyl-4-methyl-3H-thiazoline-5-carboxamide methylsulfate (Compound 18) was obtained.

m.p. 70°~74° C.

EXAMPLE 15

Following the procedure similar to that of Example 7 using Compound 18 as a material, N-(2-carboxyethyl)-2-{4-[N-(3-cyclohexyloxycarbonylpropyl)amidino]benzoylimino}-3-n-butyl-4-methyl-3H-thiazoline-5-carboxamide (Compound 19) was obtained.

m.p. 204°~204.5° C. (decomposed)

EXAMPLE 16

A mixture of Compound 18 (0.1 g), 10% aqueous sodium hydroxide solution (0.4 ml) and 2-propanol (4 ml) was stirred at room temperature for 5 hours, and adjusted to pH 5 by adding 1% aqueous phosphoric acid solution. After removal of the solvent by decantation, the oily residue was crystallized from water—acetone to give N-(2-carboxyethyl)-2-{4-[N-(3-carboxypropyl)amidino]benzoylimino}-3-n-butyl-4-methyl-3H-thiazoline-5-carboxamide (Compound 20).

$^1$H-NMR (DMSO-d$_6$) δ (ppm); 0.96 (3H, t, J=7Hz), 1.41 (2H, m), 1.65–1.85 (4H, m), 2.10–2.22 (4H, m), 2.61 (3H, s), 3.26–3.45 (4H, m), 4.33 (2H, t, J=7Hz), 7.91 (2H, d, J=8Hz), 8.29 (2H, d, J=8Hz), 8.70 (1H, brs).

EXAMPLE 17

(1) 4-Cyanobenzoyl chloride (12.5 g) was added to a solution of ammonium thiocyanate (5.8 g) in acetone (125 ml) at room temperature, followed by heating under reflux for 15 minutes. The reaction mixture was ice-cooled, and after removal of the insoluble substance by filtration, the filtrate was evaporated under reduced pressure. To the resulting residue were added toluene (125 ml) and n-hexylamine (11 ml) successively, followed by stirring for 16 hours. The reaction mixture was concentrated under reduced pressure, and the residue was chromatographed on silica gel column (ethyl acetate:methylene chloride=4:96) to give 1-(4-cyanobenzoyl)-3-n-hexylthiourea (16 g).

m.p. 95°~96° C.

(2) A mixture of 1-(4-cyanobenzoyl)-3-n-hexylthiourea (15.5 g), ethyl 2-chloroacetoacetate (22 g) and toluene (160 ml) was stirred under heating reflux with removing the water generated in the reaction for 2 hours. After cooling to room temperature, the precipitated crystals were collected by filtration to give ethyl 3-n-hexyl-2-(4-cyanobenzoylimino)-4-methyl-3H-thiazoline-5-carboxylate (19.1 g).

m.p. 127°~128° C.

(3) A mixture of ethyl 3-n-hexyl-2-(4-cyanobenzoylimino)-4-methyl-3H-thiazoline-5-carboxylate (18.5 g), 10% aqueous sodium hydroxide solution (37 ml) and acetone (200 ml) was stirred under heating reflux for an hour. The reaction mixture was concentrated under reduced pressure and acidified with 3% hydrochloric acid. The precipitated crystals were collected by filtration to give 3-n-hexyl-2-(4-cyanobenzoylimino)-4-methyl-3H-thiazoline-5-carboxylic acid (17.2 g).

m.p. 216°~218° C.

(4) A mixture of 3-n-hexyl-2-(4-cyanobenzoylimino)-4-methyl-3H-thiazoline-5-carboxylic acid (16.5 g), WSC.HCl (10.2 g), HOBt.H$_2$O (10.2 g), β-alanine-t-butyl ester hydrochloride (9.68 g), triethylamine (7.4 ml) and DMF (180 ml) was stirred at room temperature for 5.5 hours. Water (1.2 l) was added to the reaction mixture, and after extraction with methylene chloride, the organic layer was washed with a saturated aqueous sodium bicarbonate solution and a saturated aqueous sodium chloride solution and dried over magnesium sulfate. After concentration under reduced pressure, the precipitated crystals were washed with hexane to give N-(2-t-butoxycarbonylethyl)-3-n-hexyl-2-(4-cyanobenzoylimino)-4-methyl-3H-thiazoline-5-carboxamide (20.5 g).

m.p. 130°~131° C.

(5) Following the procedure similar to that of Example 14(4) using N-(2-t-butoxycarbonylethyl)-3-n-hexyl-2-(4-cyanobenzoylimino)-4-methyl-3H-thiazoline-5-carboxamide (20 g), N-(2-t-butoxycarbonylethyl)-2-(4-thiocarbamoylbenzoylimino)-3-n-hexyl-4-methyl-3H-thiazoline-5-carboxamide (21.0 g) was obtained.

m.p. 190°~190.5° C.

(6) N-(2-t-Butoxycarbonylethyl)-2-(4-thiocarbamoylbenzoylimino)-3-n-hexyl-4-methyl-3H-thiazoline-5-carboxamide (20.5 g) was dissolved in DMF (150 ml), and then dimethyl sulfate (10.9 ml) was added thereto. After stirring at room temperature for 24 hours, the reaction mixture was concentrated under reduced pressure and recrystallized from acetone—hexane to give N-(2-t-butoxycarbonylethyl)-2-[4-(methylthioimidoyl)benzoylimino]-3-n-hexyl-4-methyl-3H-thiazoline-5-carboxamide methylsulfate (11.5 g).

m.p. 197°~199° C.

(7) A mixture of N-(2-t-butoxycarbonylethyl)-2-[4-(methylthioimidoyl)benzoylimino]-3-n-hexyl-4-methyl-3H-thiazoline-5-carboxamide methylsulfate (1.5 g), 4-aminobutyric acid (0.2 g) and methanol (15 ml) was stirred under heating reflux for 3 hours. The reaction mixture was concentrated under reduced pressure, dissolved in methylene chloride, washed with a saturated aqueous sodium bicarbonate solution and a saturated aqueous sodium chloride solution and dried over magnesium sulfate. After concentration under reduced pressure, the residue was chromatographed on silica gel column (chloroform:methanol= 4:1) to give N-(2-t-butoxycarbonylethyl)-2-{4-[N-(3-carboxypropyl)amidino]benzoylimino}-3-n-hexyl-4-methyl-3H-thiazoline-5-carboxamide (Compound 21).

m.p. 119°~122° C.

EXAMPLE 18

A mixture of N-(2-t-butoxycarbonylethyl)-2-[4-(methylthioimidoyl)benzoylimino]-3-n-hexyl-4-methyl-3H-thiazoline-5-carboxamide methylsulfate (2 g) obtained in Example 17(6), methyl 4-aminobutyrate hydrochloride (0.56 g), sodium acetate (0.3 g) and methanol (20 ml) was stirred under heating reflux for 3 hours. The reaction mixture was concentrated under reduced pressure, dissolved in methylene chloride, washed with a saturated aqueous sodium bicarbonate solution and a saturated aqueous sodium chloride solution and dried over magnesium sulfate. After concentration under reduced pressure, the residue was chromatographed on silica gel column (chloroform:methanol= 9:1) to give N-(2-t-butoxycarbonylethyl)-2-{4-[N-(3-methoxycarbonylpropyl)amidino]benzoylimino}-3-n-hexyl-4-methyl-3H-thiazoline-5-carboxamide (Compound 22).

m.p. 125°~127° C.

EXAMPLE 19

Following the procedure similar to that of Example 18 using cyclohexyl 4-aminobutyrate methanesulfonate as a material, N-(2-t-butoxycarbonylethyl)-2-{4-[N-(3-cyclohexyloxycarbonylpropyl)amidino]benzoylimino}-3-n-hexyl-4-methyl-3H-thiazoline-5-carboxamide (Compound 23) was obtained.

m.p. 178°~181.5° C.

EXAMPLE 20

A mixture of Compound 21 (0.05 g) and trifluoroacetic acid (0.5 ml) was stirred at room temperature for an hour. The reaction mixture was concentrated under reduce pressure, and the residue was crystallized from ether and collected by filtration to give N-(2-carboxyethyl)-2-{4-[N-(3-carboxypropyl)amidino]benzoylimino}-3-n-hexyl-4-methyl-3H-thiazoline-5-carboxamide trifluoroacetate (Compound 24).

m.p. 151°~153° C.

EXAMPLE 21

Following the reaction procedure similar to that of Example 20, the following compounds were obtained.

N-(2-Carboxyethyl)-2-{4-[N-(3-methoxycarbonylpropyl)amidino]benzoylimino}-3-n-hexyl-4-methyl-3H-thiazoline-5-carboxamide trifluoroacetate (Compound 25)

m.p. 54°~56° C.

N-(2-Carboxyethyl)-2-{4-[N-(3-cyclohexyloxycarbonylpropyl)amidino]benzoylimino}-3-n-hexyl-4-methyl-3H-thiazoline-5-carboxamide trifluoroacetate (Compound 26)

m.p. 45°~49° C.

EXAMPLE 22

(1) 4-Cyanobenzoyl chloride (12.5 g) was added to a solution of ammonium thiocyanate (5.8 g) in acetone (125 ml) at room temperature, followed by heating under reflux for 15 minutes. The reaction mixture was ice-cooled, and after removal of the insoluble substance by filtration, the filtrate was evaporated under reduced pressure. To the resulting residue were added toluene (125 ml) and n-tetradecylamine (17.7 g) successively, followed by stirring for an hour. The reaction mixture was concentrated under reduced pressure, and the residue was chromatographed on silica gel column (ethyl acetate:methylene chloride=2:98) to give 1-(4-cyanobenzoyl)-3-n-tetradecylthiourea (21.4 g).

m.p. 78°~80° C.

(2) A mixture of 1-(4-cyanobenzoyl)-3-n-tetradecylthiourea (21 g), ethyl 2-chloroacetoacetate (25 g) and toluene (240 ml) was stirred under heating reflux with removing the water generated in the reaction for 5 hours. After cooling to room temperature, the precipitated crystals were collected by filtration to give ethyl 3-n-tetradecyl-2-(4-cyanobenzoylimino)-4-methyl-3H-thiazoline-5-carboxylate (23.4 g).

m.p. 86°~86.5° C.

(3) A mixture of ethyl 3-n-tetradecyl-2-(4-cyanobenzoylimino)-4-methyl-3H-thiazoline-5-carboxylate (23 g), 10% aqueous sodium hydroxide solution (36 ml) and acetone (250 ml) was stirred under heating reflux for an hour. The reaction mixture was concentrated under reduced pressure and acidified with 3% hydrochloric acid. The precipitated crystals were collected by filtration to give 3-n-tetradecyl-2-(4-cyanobenzoylimino)-4-methyl-3H-thiazoline-5-carboxylic acid (21.7 g).

m.p. 176°~177° C.

(4) A mixture of 3-n-tetradecyl-2-(4-cyanobenzoylimino)-4-methyl-3H-thiazoline-5-carboxylic acid (21 g), WSC.HCl (10.0 g), HOBt.H$_2$O (10.0 g), β-alanine-t-butyl ester hydrochloride (9.46 g), triethylamine (7.3 ml) and DMF (200 ml) was stirred at room temperature for 5 hours. Water (1.2 l) was added to the reaction mixture, and after extraction with methylene chloride, the organic layer was washed with a saturated aqueous sodium bicarbonate solution and a saturated aqueous sodium chloride solution and dried over magnesium sulfate. After concentration under reduced pressure, the resulting crude crystals were washed with hexane to give N-(2-t-butoxycarbonylethyl)-3-n-tetradecyl-2-(4-cyanobenzoylimino)-4-methyl-3H-thiazoline- 5-carboxamide (25.1 g).

m.p. 92.5°~94° C.

(5) Following the procedure similar to that of Example 14(4) using N-(2-t-butoxycarbonylethyl)-3-n-tetradecyl-2-(4-cyanobenzoylimino)-4-methyl-3H-thiazoline-5-carboxamide (20 g), N-(2-t-butoxycarbonylethyl)-2-(4-thiocarbamoylbenzoylimino)-3-n-tetradecyl-4-methyl-3H-thiazoline-5-carboxamide (25.5 g) was obtained.

m.p. 150°~152.5° C.

(6) N-(2-t-Butoxycarbonylethyl)-2-(4-thiocarbamoylbenzoylimino)-3-n-tetradecyl-4-methyl-3H-thiazoline-5-carboxamide (25 g) was dissolved in DMF (150 ml), and then dimethyl sulfate (11 ml) was added thereto. After stirring at room temperature for 5 hours, the reaction mixture was concentrated under reduced pressure to give N-(2-t-butoxycarbonylethyl)-2-[4-(methylthioimidoyl) benzoylimino]-3-n-tetradecyl-4-methyl-3H-thiazoline-5-carboxamide methylsulfate (32 g).

$^1$H-NMR (DMSO-d$_6$) δ (ppm); 0.85 (3H, t, J=6Hz), 1.0–1.5 (22H, m), 1.42 (9H, s), 1.75 (2H, m), 2.48 (2H, t, J=6Hz), 2.62 (3H, s), 2.88 (3H, s), 3.40 (3H, s), 3.42 (2H, q, J=6Hz), 4.36 (2H, m), 7.98 (2H, d, J=8Hz), 8.34 (1H, t, J=6Hz), 8.39 (2H, d, J=6Hz)

(7) A mixture of N-(2-t-butoxycarbonylethyl)-2-[4-(methylthioimidoyl)benzoylimino]-3-n-tetradecyl-4-methyl-3H-thiazoline-5-carboxamide methylsulfate (2 g), 4-aminobutyric acid (0.32 g) and methanol (20 ml) was stirred under heating reflux for 1.5 hours. The reaction mixture was concentrated under reduced pressure, dissolved in methylene chloride, washed with a saturated aqueous sodium bicarbonate solution and a saturated aqueous sodium chloride solution and dried over magnesium sulfate. After concentration under reduced pressure, the residue was chromatographed on silica gel column (chloroform:methanol= 4:1) to give N-(2-t-butoxycarbonylethyl)-2-{4-[N-(3-carboxypropyl)amidino]benzoylimino}-3-n-tetradecyl-4-methyl-3H-thiazoline-5-carboxamide (Compound 27).

m.p. 177°~179° C.

EXAMPLE 23

A mixture of N-(2-t-butoxycarbonylethyl)-2-[4-(methylthioimidoyl)benzoylimino]-3-n-tetradecyl-4-methyl-3H-thiazoline-5-carboxamide methylsulfate (2 g) obtained in Example 22(6), methyl 4-aminobutyrate hydrochloride (0.48 g), sodium acetate (0.3 g) and methanol (20 ml) was stirred under heating reflux for 3 hours. The reaction mixture was concentrated under reduced pressure, dissolved in methylene chloride, washed with a saturated aqueous sodium bicarbonate solution and a saturated aqueous sodium chloride solution and dried over magnesium sulfate. After concentration under reduced pressure, the residue was chromatographed on silica gel column (chloroform:methanol= 9:1) to give N-(2-t-butoxycarbonylethyl)-2-{4-[N-(3-methoxycarbonylpropyl)amidino]benzoylimino}-3-n-tetradecyl-4-methyl-3H-thiazoline-5-carboxamide (Compound 28).

m.p. 81°~84° C.

EXAMPLE 24

Following the procedure similar to that of Example 23 using cyclohexyl 4-aminobutyrate methanesulfonate as a material, N-(2-t-butoxycarbonylethyl)-2-{4-[N-(3-cyclohexyloxycarbonylpropyl)amidino]benzoylimino}-3-n-tetradecyl-4-methyl-3H-thiazoline-5-carboxamide (Compound 29) was obtained.

m.p. 97°~98° C.

EXAMPLE 25

Following the procedure similar to that of Example 20 using each of Compounds 27, 28 and 29 as materials, the following compounds were obtained.

N-(2-Carboxyethyl)-2-{4-[N-(3-carboxypropyl)amidino]benzoylimino}-3-n-tetradecyl-4-methyl-3H-thiazoline-5-carboxamide trifluoroacetate (Compound 30)

m.p. 95°~98° C.

N-(2-Carboxyethyl)-2-{4-[N-(3-methoxycarbonylpropyl)amidino]benzoylimino}-3-n-tetradecyl-4-methyl-3H-thiazoline-5-carboxamide trifluoroacetate (Compound 31)

m.p. 127°~129° C.

N-(2-Carboxyethyl)-2-{4-[N-(3-cyclohexyloxycarbonylpropyl)amidino]benzoylimino}-3-n-tetradecyl-4-methyl-3H-thiazoline-5-carboxamide trifluoroacetate (Compound 32)

m.p. 130.5°~131.5° C.

EXAMPLE 26

(1) 4-Cyanobenzoylisothiocyanate (8 g) obtained in Example 9(1) was suspended in toluene (50 ml), and then benzylamine (4.6 ml) was added thereto, followed by stirring for 30 minutes. After addition of ethyl 2-chloroacetoacetate (14 ml), the mixture was stirred under heating reflux with removing the water generated in the reaction for 30 minutes. After cooling to room temperature, the precipitated crystals were collected by filtration to give ethyl 3-benzyl-2-(4-cyanobenzoylimino)-4-methyl-3H-thiazoline-5-carboxylate (11 g).

m.p. 189°~195.5° C.

(2) A mixture of ethyl 3-benzyl-2-(4-cyanobenzoylimino)-4-methyl-3H-thiazoline-5-carboxylate (10.8 g), 10% aqueous sodium hydroxide solution (42.5 ml), methylene chloride (150 ml) and methanol (150 ml) was stirred at room temperature for 20 minutes, under heating reflux for an hour and then at room temperature overnight. The reaction mixture was concentrated under reduced pressure, and the resulting crude crystals were washed with acetone to give sodium 3-benzyl-2-(4-cyanobenzoylimino)-4-methyl-3H-thiazoline-5-carboxylate (10.3 g).

A mixture of sodium 3-benzyl-2-(4-cyanobenzoylimino)-4-methyl-3H-thiazoline-5-carboxylic acid (10 g), WSC.HCl (5.3 g), HOBt.H$_2$O (4.2 g), β-alanine methyl ester hydrochloride (3.9 g) and DMF (100 ml) was stirred at room temperature for 24 hours. Water (1.2 l) was added to the reaction mixture, and after extraction with methylene chloride, the organic layer was washed with 3% hydrochloric acid, a saturated aqueous sodium bicarbonate solution and a saturated aqueous sodium chloride solution and dried over magnesium sulfate. After concentration under reduced pressure, the resulting crude crystals were recrystallized from methanol to give N-(2-methoxycarbonylethyl)-3-benzyl-2-(4-cyanobenzoylimino)-4-methyl-3H-thiazoline-5-carboxamide (8.7 g).

m.p. 191.5°~194.5° C.

(3) A mixture of N-(2-methoxycarbonylethyl)-3-benzyl-2-(4-cyanobenzoylimino)-4-methyl-3H-thiazoline-5-carboxamide (8.6 g), sodium hydrosulfide (70%, 3.0 g), magnesium chloride hexahydrate (3.8 g) and DMF (80 ml) was stirred at room temperature overnight. After addition of water (300 ml), the precipitated crystals were collected by filtration, and the resulting crude crystals were washed with 3% hydrochloric acid to give N-(2-methoxycarbonylethyl)-2-(4-thiocarbamoylbenzoylimino)-3-benzyl-4-methyl-3H-thiazoline-5-carboxamide (9.3 g).

m.p. 187°~189.5° C.

(4) N-(2-Methoxycarbonylethyl)-2-(4-thiocarbamoylbenzoylimino)-3-benzyl-4-methyl-3H-thiazoline-5-carboxamide (9.2 g) was suspended in DMF (50 ml), and then dimethyl sulfate (5.2 ml) was added thereto, followed by stirring at 60° C. for 4.5 hours. After cooling to room temperature, acetone (200 ml) was added, and the precipitated crystals were collected by filtration to give N-(2-methoxycarbonylethyl)-2-[4-(methylthioimidoyl)benzoylimino]-3-benzyl-4-methyl-3H-thiazoline-5-carboxamide methylsulfate (9.4 g).

m.p. 187°~189.5° C.

(5) Following the procedure similar to that of Example 2 using N-(2-methoxycarbonylethyl)-2-[4-(methylthioimidoyl)benzoylimino]-3-benzyl-4-methyl-3H-thiazoline-5-carboxamide methylsulfate (1 g), N-(2-methoxycarbonylethyl)-2-{4-[N-(3-methoxycarbonylpropyl)amidino]benzoylimino}-3-benzyl- 4-methyl-3H-thiazoline-5-carboxamide methylsulfate (0.78 g) (Compound 33) was obtained.

m.p. 116.5°~118° C.

EXAMPLE 27

Following the procedure similar to that of Example 3 using N-(2-methoxycarbonylethyl)-2-[4-(methylthioimidoyl)benzoylimino]-3-benzyl-4-methyl-3H-thiazoline-5-carboxamide methylsulfate (1 g) obtained in Example 26(4), N-(2-methoxycarbonylethyl)-2-{4-[N-(3-cyclohexyloxycarbonylpropyl)amidino]benzoylimino}-3-benzyl-4-methyl-3H-thiazoline-5-carboxamide methylsulfate (Compound 34) was obtained.

m.p. 118.5°~121° C.

EXAMPLE 28

A mixture of Compound 33 (0.5 g), 10% aqueous sodium hydroxide solution (2 ml), water (5 ml) and 2-propanol (20 ml) was stirred at room temperature for 5 hours, and adjusted to pH 5 by adding 1% aqueous phosphoric acid solution. After removal of the solvent by decantation, the oily residue was crystallized from water—acetone to give N-(2-carboxyethyl)-2-{4-[N-(3-carboxypropyl)amidino]benzoylimino}-3-benzyl-4-methyl-3H-thiazoline-5-carboxamide (Compound 35).

m.p. 159°~163° C.

EXAMPLE 29

Following the procedure similar to that of Example 7 using Compound 34 as a material, N-(2-carboxyethyl)-2-{4-[N-(3-cyclohexyloxycarbonylpropyl)amidino]benzoylimino}-3-benzyl-4-methyl-3H-thiazoline-5-carboxamide (Compound 36) was obtained.

m.p. 191°~193° C.

EXAMPLE 30

(1) 4-Cyanobenzoyl chloride (12.5 g) was added to a solution of ammonium thiocyanate (5.8 g) in acetone (125 ml) at room temperature, followed by heating under reflux for 15 minutes. The reaction mixture was ice-cooled, and after removal of the insoluble substance by filtration, the filtrate was evaporated under reduced pressure. To the resulting residue were added toluene (125 ml) and 2-phenylethylamine (10.4 g) successively, followed by stirring for 2 hours. The reaction mixture was concentrated under reduced pressure, and the resulting crude crystals were washed with ethyl acetate to give 1-(4-cyanobenzoyl)-3-(2-phenylethyl)thiourea (14.1 g).

m.p. 142°~143.5° C.

(2) A mixture of 1-(4-cyanobenzoyl)-3-(2-phenylethyl)thiourea (13.5 g), ethyl 2-chloroacetoacetate (18 g) and toluene (150 ml) was stirred under heating reflux with removing the water generated in the reaction for 4 hours. After cooling to room temperature, the precipitated crystals were collected by filtration to give ethyl 3-(2-phenylethyl)-2-(4-cyanobenzoylimino)-4-methyl-3H-thiazoline-5-carboxylate (14.3 g).

m.p. 195.5°~197.5° C.

(3) A mixture of ethyl 3-(2-phenylethyl)-2-(4-cyanobenzoylimino)-4-methyl-3H-thiazoline-5-carboxylate (13.5 g), 10% aqueous sodium hydroxide solution (26 ml) and acetone (150 ml) was stirred under heating reflux for 2 hours. The reaction mixture was concentrated under reduced pressure and acidified with 3% hydrochloric acid. The precipitated crystals were collected by filtration to give 3-(2-phenylethyl)-2-(4-cyanobenzoylimino)-4-methyl-3H-thiazoline-5-carboxylic acid (11.9 g).

m.p. 232°~233° C.

(4) A mixture of 3-(2-phenylethyl)-2-(4-cyanobenzoylimino)-4-methyl-3H-thiazoline-5-carboxylic acid (11.5 g), WSC.HCl (8.5 g), HOBt.H$_2$O (6.8 g), β-alanine-t-butyl ester hydrochloride (6.4 g), triethylamine (4.9 ml) and DMF (200 ml) was stirred at room temperature for 5 hours. Water (1.2 l) was added to the reaction mixture, and after extraction with methylene chloride, the organic layer was washed with a saturated aqueous sodium bicarbonate solution and a saturated aqueous sodium chloride solution and dried over magnesium sulfate. After concentration under reduced pressure, the resulting crude crystals were recrystallized from ethyl acetate—hexane to give N-(2-t-butoxycarbonylethyl)-3-(2-phenylethyl)-2-(4-cyanobenzoylimino)-4-methyl-3H-thiazoline-5-carboxamide (15.9 g).

m.p. 101°~102° C.

(5) Following the procedure similar to that of Example 14(4) using N-(2-t-butoxycarbonylethyl)-3-(2-phenylethyl)-2-(4-cyanobenzoylimino)-4-methyl-3H-thiazoline-5-carboxamide (15.5 g), N-(2-t-butoxycarbonylethyl)- 2-(4-thiocarbamoylbenzoylimino)-3-(2-phenylethyl)-4-methyl-3H-thiazoline-5-carboxamide (14.1 g) was obtained.

m.p. 220°~221° C.

(6) N-(2-t-Butoxycarbonylethyl)-2-(4-thiocarbamoylbenzoylimino)-3-(2-phenylethyl)-4-methyl-3H-thiazoline-5-carboxamide (13.5 g) was dissolved in DMF (100 ml), and then dimethyl sulfate (11 ml) was added thereto. After stirring at room temperature for 18 hours, the reaction mixture was concentrated under reduced pressure, and the residue was recrystallized from acetone—hexane to give N-(2-t-butoxycarbonylethyl)-2-[4-(methylthioimidoyl)benzoylimino]-3-(2-phenylethyl)-4-methyl-3H-thiazoline-5-carboxamide methylsulfate (12.0 g).

m.p. 162.5°~164.5° C.

(7) A mixture of N-(2-t-butoxycarbonylethyl)-2-[4-(methylthioimidoyl)benzoylimino]-3-(2-phenylethyl)-4-methyl-3H-thiazoline-5-carboxamide methylsulfate (2 g), 4-aminobutyric acid (0.32 g) and methanol (20 ml) was stirred under heating reflux for 2.5 hours. The reaction mixture was concentrated under reduced pressure, dissolved in methylene chloride, washed with a saturated aqueous sodium bicarbonate solution and a saturated aqueous sodium chloride solution and dried over magnesium sulfate. After concentration under reduced pressure, the residue was chromatographed on silica gel column (chloroform:methanol= 4:1) to give N-(2-t-butoxycarbonylethyl)-2-{4-[N-(3-carboxypropyl)amidino]benzoylimino}-3-(2-phenylethyl)-4-methyl-3H-thiazoline-5-carboxamide (Compound 37).

m.p. 74°~77° C.

EXAMPLE 31

A mixture of N-(2-t-butoxycarbonylethyl)-2-[4-(methylthioimidoyl)benzoylimino]-3-(2-phenylethyl)-4-methyl-3H-thiazoline-5-carboxamide methylsulfate (2 g) obtained in Example 30(6), methyl 4-aminobutyrate hydrochloride (0.5 g), sodium acetate (0.3 g) and methanol (20 ml) was stirred under heating reflux for 3 hours. The reaction mixture was concentrated under reduced pressure, dissolved in methylene chloride, washed with a saturated aqueous sodium bicarbonate solution and a saturated aqueous sodium chloride solution and dried over magnesium sulfate. After concentration under reduced pressure, the residue was chromatographed on silica gel column (chloroform:methanol= 9:1) to give N-(2-t-butoxycarbonylethyl)-2-{4-[N-(3-methoxycarbonylpropyl)amidino]benzoylimino}-3-(2-phenylethyl)-4-methyl-3H-thiazoline-5-carboxamide (Compound 38).

m.p. 84°~88° C.

EXAMPLE 32

Following the procedure similar to that of Example 31 using cyclohexyl 4-aminobutyrate methanesulfonate as a material, N-(2-t-butoxycarbonylethyl)-2-{4-[N-(3-cyclohexyloxycarbonylpropyl)amidino]benzoylimino}-3-(2-phenylethyl)-4-methyl-3H-thiazoline-5-carboxamide (Compound 39) was obtained.

m.p. 42°~46° C.

EXAMPLE 33

Following the procedure similar to that of Example 20 using each of Compounds 30 to 32 as materials, the following compounds were obtained.

N-(2-Carboxyethyl)-2-{4-[N-(3-carboxypropyl)amidino]benzoylimino}-3-(2-phenylethyl)-4-methyl-3H-thiazoline-5-carboxamide trifluoroacetate (Compound 40)

m.p. 131°~134° C.

N-(2-Carboxyethyl)-2-{4-[N-(3-methoxycarbonylpropyl)amidino]benzoylimino}-3-(2-phenylethyl)-4-methyl-3H-thiazoline-5-carboxamide trifluoroacetate (Compound 41)

m.p. 115°~118° C.

N-(2-Carboxyethyl)-2-{4-[N-(3-cyclohexyloxycarbonylpropyl)amidino]benzoylimino}-3-(2-phenylethyl)-4-methyl-3H-thiazoline-5-carboxamide trifluoroacetate (Compound 42)

m.p. 62°~65° C.

EXAMPLE 34

(1) 4-Cyanobenzoyl chloride (20 g) was added in portions to a solution of ammonium thiocyanate (9.2 g) in acetone (200 ml) at room temperature, followed by heating under reflux for 20 minutes. The reaction mixture was ice-cooled, and after removal of the insoluble substance by filtration, the filtrate was evaporated under reduced pressure. To the resulting residue were added toluene (100 ml) and cyclopropylamine (7.6 g) successively, followed by stirred for 30 minutes. The precipitated crystals were collected by filtration and recrystallized from ethyl acetate to give 1-(4-cyanobenzoyl)-3-cyclopropylthiourea (20 g) as a colorless powder.

m.p. 151°~152° C.

(2) A mixture of 1-cyclopropyl-3-(4-cyanobenzoyl)thiourea (19.5 g), ethyl 2-chloroacetoacetate (24.2 ml) and toluene (200 ml) was stirred under heating reflux with removing the water generated in the reaction for 2 hours. After cooling to room temperature, the precipitated crystals were collected by filtration to give ethyl 3-cyclopropyl-2-(4-cyanobenzoylimino)-4-methyl-3H-thiazoline-5-carboxylate (26.7 g).

m.p. 224.5°~225.5° C.

(3) A mixture of ethyl 3-cyclopropyl-2-(4-cyanobenzoylimino)-4-methyl-3H-thiazoline-5-carboxylate (26.3 g), 10% aqueous sodium hydroxide solution (44 ml) and acetone (300 ml) was stirred under heating reflux for 2.5 hours. After cooling to room temperature, the precipitated crystals were collected by filtration to give sodium 3-cyclopropyl-2-(4-cyanobenzoylimino)-4-methyl-3H-thiazoline-5-carboxylate (26.4 g).

m.p. 273°~274° C. (decomposed)

(4) A mixture of sodium 3-cyclopropyl-2-(4-cyanobenzoylimino)-4-methyl-3H-thiazoline-5-carboxylate (26 g), DMC (18.9 g), β-alanine methyl ester hydrochloride (15.6 g), triethylamine (31 ml) and DMF (300 ml) was stirred at room temperature for 3 hours. After addition of water (1.2 l), the precipitated crystals were collected by filtration, and the resulting crude crystals were dissolved in methylene chloride. The insoluble substance was filtered off using celite, and the mother liquor was concentrated under reduced pressure to give N-(2-methoxycarbonylethyl)-3-cyclopropyl-2-(4-cyanobenzoylimino)-4-methyl-3H-thiazoline-5-carboxamide (22.7 g).

m.p. 197.5°~198.5° C.

(5) Following the procedure similar to that of Example 14(4) using N-(2-methoxycarbonylethyl)-3-cyclopropyl-2-(4-cyanobenzoylimino)-4-methyl-3H-thiazoline-5-carboxamide (22 g), N-(2-methoxycarbonylethyl)-2-(4-thiocarbamoylbenzoylimino)-3-cyclopropyl-4-methyl-3H-thiazoline-5-carboxamide (21.9 g) was obtained.

m.p. 215°~215.5° C.

(6) N-(2-Methoxycarbonylethyl)-2-(4-thiocarbamoylbenzoylimino)-3-cyclopropyl-4-methyl-3H-thiazoline-5-carboxamide (21 g) was suspended in DMF (150 ml), and after heating to 50° C., dimethyl sulfate (7.7 ml) was added dropwise over a 5-minute period. After stirring at 55° C. for 2 hours, acetone (500 ml) was added, followed by cooling to room temperature. Hexane (400 ml) was added to the reaction mixture, and the precipitated crystals were collected by filtration to give N-(2-methoxycarbonylethyl)-2-[4-(methylthioimidoyl)benzoylimino]-3-cyclopropyl-4-methyl-3H-thiazoline-5-carboxamide methylsulfate (24.5 g).

m.p. 173.5°~174.5° C. (decomposed)

(7) N-(2-Methoxycarbonylethyl)-2-[4-(methylthioimidoyl)benzoylimino]-3-cyclopropyl-4-methyl-3H-thiazoline-5-carboxamide methylsulfate (3.0 g) was added to a mixture of methyl 4-aminobutyrate hydrochloride (1.45 g), sodium acetate (620 mg) and methanol (30 ml) under heating reflux, and the reaction mixture was heated under reflux for an hour. After evaporation of the methanol under reduced pressure, the residue was dissolved in methylene chloride and washed with water. After evaporation of the solvent, methanol and isopropyl ether were added to the residue, and the solvent was separated by decantation. The residue was dissolved in methylene chloride again. The solution was neutralized with a saturated aqueous sodium bicarbonate solution, and evaporated to give N-(2-methoxycarbonylethyl)-2-{4-[N-(3-methoxycarbonylpropyl)amidino]benzoylimino}-3-cyclopropyl-4-methyl-3H-thiazoline-5-carboxamide (Compound 43).

m.p. 57°~58° C.

EXAMPLE 35

Following the procedure similar to that of Example 9(8) using N-(2-methoxycarbonylethyl)-2-[4-(methylthioimidoyl)benzoylimino]-3-cyclopropyl-4-methyl-3H-thiazoline-5-carboxamide methylsulfate obtained in Example 34(6) and cyclohexyl 4-aminobutyrate methanesulfonate, N-(2-methoxycarbonylethyl)-2-{4-[N-(3-cyclohexyloxycarbonylpropyl)amidino]benzoylimino}-

3-cyclopropyl-4-methyl-3H-thiazoline-5-carboxamide methylsulfate (Compound 44) was obtained.

m.p. 82°~84° C.

EXAMPLE 36

Following the procedure similar to that of Example 4 using N-(2-methoxycarbonylethyl)-2-[4-(methylthioimidoyl)benzoylimino]-3-cyclopropyl-4-methyl-3H-thiazoline-5-carboxamide methylsulfate obtained in Example 34(6) and 4-amino-N-cyclohexylbutyramide hydrochloride, N-(2-methoxycarbonylethyl)-2-{4-[N-(3-cyclohexylaminocarbonylpropyl)amidino]benzoylimino}-3-cyclopropyl-4-methyl-3H-thiazoline-5-carboxamide methylsulfate (Compound 45) was obtained.

$^1$H-NMR (DMSO-$d_6$) δ (ppm); 1.0–1.8 (16H, m), 2.23 (2H, t, J=6Hz), 2.58 (2H, t, J=6Hz), 2.67 (3H, s), 3.36 (3H, s), 3.45 (4H, q, J=6Hz), 3.61 (3H, s), 7.83 (1H, t, J=6Hz), 7.87 (2H, d, J=8Hz), 8.27 (1H, t, J=6Hz), 8.36 (2H, d, J=8Hz), 9.42 (2H, br).

EXAMPLE 37

Following the procedure similar to that of Example 4 using N-(2-methoxycarbonylethyl)-2-[4-(methylthioimidoyl)benzoylimino]-3-cyclopropyl-4-methyl-3H-thiazoline-5-carboxamide methylsulfate obtained in Example 34(6) and 6-aminocaproanilide hydrochloride, N-(2-methoxycarbonylethyl)-2-{4-[N-(5-phenylaminocarbonylpentyl)amidino]benzoylimino}-3-cyclopropyl-4-methyl-3H-thiazoline-5-carboxamide methylsulfate (Compound 46) was obtained.

$^1$H-NMR (DMSO-$d_6$) δ (ppm); 1.1–1.5 (6H, m), 1.69 (4H, m), 2.35 (2H, t, J=6Hz), 2.58 (2H, t, J=6Hz), 2.66 (3H, s), 3.37 (3H, s), 3.45 (4H, q, J=6Hz), 3.61 (3H, s), 7.01 (1H, t, J=6Hz), 7.28 (2H, t, J=8Hz), 7.61 (2H, d, J=8Hz), 7.85 (2H, d, J=8Hz), 8.30 (1H, t, J=6Hz), 8.35 (2H, d, J=8Hz), 9.97 (1H, s).

EXAMPLE 38

Following the procedure similar to that of Example 11 using N-(2-methoxycarbonylethyl)-2-[4-(methylthioimidoyl)benzoylimino]-3-cyclopropyl-4-methyl-3H-thiazoline-5-carboxamide methylsulfate obtained in Example 34(6), N-(2-methoxycarbonylethyl)-2-{4-[N-(3-carboxypropyl)amidino]benzoylimino}-3-cyclopropyl-4-methyl-3H-thiazoline-5-carboxamide methylsulfate (Compound 47) was obtained.

m.p. 67°~72° C.

EXAMPLE 39

Following the procedure similar to that of Example 12 using Compound 43, N-(2-carboxyethyl)-2-{4-[N-(3-carboxypropyl)amidino]benzoylimino}-3-cyclopropyl-4-methyl-3H-thiazoline-5-carboxamide (Compound 48) was obtained.

m.p. 256°~256.5° C.

EXAMPLE 40

Following the procedure similar to that of Example 7 using Compound 44, N-(2-carboxyethyl)-2-{4-[N-(3-cyclohexyloxycarbonylpropyl)amidino]benzoylimino}-3-cyclopropyl-4-methyl-3H-thiazoline-5-carboxamide (Compound 49) was obtained.

m.p. 199°~201° C.

EXAMPLE 41

Following the procedure similar to that of Example 8 using Compound 45, N-(2-carboxyethyl)-2-{4-[N-(3-cyclohexylaminocarbonylpropyl)amidino]benzoylimino}-3-cyclopropyl-4-methyl-3H-thiazoline-5-carboxamide (Compound 50) was obtained.

m.p. 147°~149° C.

EXAMPLE 42

Following the procedure similar to that of Example 8 using Compound 46, N-(2-carboxyethyl)-2-{4-[N-(5-phenylaminocarbonylpentyl)amidino]benzoylimino}-3-cyclopropyl-4-methyl-3H-thiazoline-5-carboxamide (Compound 51) was obtained.

m.p. 150°~154° C.

EXAMPLE 43

(1) 4-Cyanobenzoyl chloride (5.8 g) was added in portions to a solution of ammonium thiocyanate (2.7 g) in acetone (50 ml) at room temperature, followed by heating under reflux for 10 minutes. The reaction mixture was ice-cooled, and after removal of the insoluble substance by filtration, the filtrate was evaporated under reduced pressure. To the resulting residue were added toluene (30 ml) and cyclobutylamine (3 ml) successively, followed by stirred for 20 minutes. To the reaction mixture was added ethyl 2-chloroacetoacetate (11.6 ml), followed by heating under reflux with removing the water generated in the reaction for 100 minutes. The reaction mixture was allowed to stand for cooling, and the precipitated crystals were collected by filtration to give ethyl 2-(4-cyanobenzoylimino)-3-cyclobutyl-4-methyl-3H-thiazoline-5-carboxylate.

m.p. 221.5°~223° C. (decomposed)

(2) A mixture of ethyl 2-(4-cyanobenzoylimino)-3-cyclobutyl-4-methyl-3H-thiazoline-5-carboxylate (8 g), 10% aqueous sodium hydroxide solution (13 ml) and acetone (100 ml) was stirred under heating reflux for 2 hours. After cooling to room temperature, conc. hydrochloric acid (2.8 ml) was added thereto, and the precipitated crystals were collected by filtration to give 2-(4-cyanobenzoylimino)-3-cyclobutyl-4-methyl-3H-thiazoline-5-carboxylic acid (8.6 g).

m.p. 231°~234° C. (decomposed)

(3) Following the procedure similar to that of Example 36(4) using 2-(4-cyanobenzoylimino)-3-cyclobutyl-4-methyl-3H-thiazoline-5-carboxylic acid (8.6 g), N-(2-methoxycarbonylethyl)-2-(4-cyanobenzoylimino)-3-cyclobutyl-4-methyl-3H-thiazoline-5-carboxamide was obtained.

m.p. 158.5°~159.5° C.

(4) Following the procedure similar to that of Example 14(4) using N-(2-methoxycarbonylethyl)-2-(4-cyanobenzoylimino)-3-cyclobutyl-4-methyl-3H-thiazoline-5-carboxamide, N-(2-methoxycarbonylethyl)-2-(4-thiocarbamoylbenzoylimino)-3-cyclobutyl-4-methyl-3H-thiazoline-5-carboxamide was obtained.

m.p. 196.5°~197° C. (decomposed)

(5) Following the procedure similar to that of Example 34(6) using N-(2-methoxycarbonylethyl)-2-(4-thiocarbamoylbenzoylimino)-3-cyclobutyl-4-methyl-3H-thiazoline-5-carboxamide obtained above, N-(2-methoxycarbonylethyl)-2-[4-(methylthioimidoyl)benzoylimino]-3-cyclobutyl-4-methyl-3H-thiazoline-5-carboxamide methylsulfate was obtained.

m.p. 162°~165° C. (decomposed)

(6) Following the procedure similar to that of Example 34(7) using N-(2-methoxycarbonylethyl)-2-[4-(methylthioimidoyl)benzoylimino]-3-cyclobutyl-4-methyl-3H-thiazoline-5-carboxamide methylsulfate, N-(2-methoxycarbonylethyl)-2-{4-[N-(3-methoxycarbonylpropyl)amidino]benzoylimino}-3-cyclobutyl-4-methyl-3H-thiazoline-5-carboxamide (Compound 52) was obtained.

m.p. 72°~75° C.

EXAMPLE 44

Following the procedure similar to that of Example 9(8) using N-(2-methoxycarbonylethyl)-2-[4-(methylthioimidoyl)benzoylimino]-3-cyclobutyl-4-methyl-3H-thiazoline-5-carboxamide methylsulfate obtained in Example 43(5) and cyclohexyl 4-aminobutyrate methanesulfonate, N-(2-methoxycarbonylethyl)-2-{4-[N-(3-cyclohexyloxycarbonylpropyl)amidino]benzoylimino}-3-cyclobutyl-4-methyl-3H-thiazoline-5-carboxamide methylsulfate (Compound 53) was obtained.

m.p. 239°~240° C.

EXAMPLE 45

Following the procedure similar to that of Example 11 using N-(2-methoxycarbonylethyl)-2-[4-(methylthioimidoyl)benzoylimino]-3-cyclobutyl-4-methyl-3H-thiazoline-5-carboxamide methylsulfate obtained in Example 43(5), N-(2-methoxycarbonylethyl)-2-{4-[N-(3-carboxypropyl)amidino]benzoylimino}-3-cyclobutyl-4-methyl-3H-thiazoline-5-carboxamide methylsulfate (Compound 54) was obtained.

m.p. 65°~70° C.

EXAMPLE 46

Following the procedure similar to that of Example 12 using Compound 52, N-(2-carboxyethyl)-2-{4-[N-(3-carboxypropyl)amidino]benzoylimino}-3-cyclobutyl-4-methyl-3H-thiazoline-5-carboxamide (Compound 55) was obtained.

m.p. 122°~124° C.

EXAMPLE 47

Following the procedure similar to that of Example 34(7) using Compound 53, N-(2-carboxyethyl)-2-{4-[N-(3-cyclohexyloxycarbonylpropyl)amidino]benzoylimino}-3-cyclobutyl-4-methyl-3H-thiazoline-5-carboxamide (Compound 56) was obtained.

m.p. 91°~93° C.

EXAMPLE 48

(1) Following the reaction procedure similar to that of Example 43(1) using cyclopentylamine in place of cyclobutylamine, ethyl 2-(4-cyanobenzoylimino)-3-cyclopentyl-4-methyl-3H-thiazoline-5-carboxylate was obtained.

m.p. 191.5°~192° C. (decomposed)

(2) A mixture of ethyl 2-(4-cyanobenzoylimino)-3-cyclopentyl-4-methyl-3H-thiazoline-5-carboxylate (35.5 g), 10% aqueous sodium hydroxide solution (55 ml) and acetone (400 ml) was stirred under heating reflux for an hour, and after cooling to room temperature, conc. hydrochloric acid (3.8 ml) was added thereto. To the reaction mixture were added HOBt.H$_2$O (17 g), β-alanine methyl ester hydrochloride (15.4 g), WSC.HCl (21.3 g), water (100 ml), DMF (400 ml) and methylene chloride (500 ml) successively, followed by stirring at room temperature for 5 hours. Water (1 l) was added to the reaction mixture, and the separated organic layer was washed with 3% hydrochloric acid, a saturated aqueous sodium bicarbonate solution and a saturated aqueous sodium chloride solution. After drying (magnesium sulfate), purification by silica gel column chromatography (methylene chloride—ethyl acetate) gave N-(2-methoxycarbonylethyl)-3-cyclopentyl-2-(4-cyanobenzoylimino)-4-methyl-3H-thiazoline-5-carboxamide.

m.p. 149.5°~150.5° C.

(3) Following the procedure similar to that of Example 14(4) using N-(2-methoxycarbonylethyl)-3-cyclopentyl-2-(4-cyanobenzoylimino)-4-methyl-3H-thiazoline-5-carboxamide, N-(2-methoxycarbonylethyl)-2-[4-thiocarbamoylbenzoylimino]-3-cyclopentyl-4-methyl-3H-thiazoline-5-carboxamide was obtained.

m.p. 149°~150° C.

(4) Following the procedure similar to that of Example 34(6) using N-(2-methoxycarbonylethyl)-2-[4-thiocarbamoylbenzoylimino]-3-cyclopentyl-4-methyl-3H-thiazoline-5-carboxamide, N-(2-methoxycarbonylethyl)-2-[4-(methylthioimidoyl)benzoylimino]-3-cyclopentyl-4-methyl-3H-thiazoline-5-carboxamide methylsulfate was obtained.

m.p. 186°~187° C. (decomposed)

(5) Following the procedure similar to that of Example 36(7) using N-(2-methoxycarbonylethyl)-2-[4-(methylthioimidoyl)benzoylimino]-3-cyclopentyl-4-methyl-3H-thiazoline-5-carboxamide methylsulfate, N-(2-methoxycarbonylethyl)-2-{4-[N-(3-methoxycarbonylpropyl)amidino]benzoylimino}-3-cyclopentyl-4-methyl-3H-thiazoline-5-carboxamide (Compound 57) was obtained.

m.p. 65°~70° C.

EXAMPLE 49

Following the procedure similar to that of Example 9(8) using N-(2-methoxycarbonylethyl)-2-[4-(methylthioimidoyl)benzoylimino]-3-cyclopentyl-4-methyl-3H-thiazoline-5-carboxamide methylsulfate obtained in Example 48(4) and cyclohexyl 4-aminobutyrate methanesulfonate, N-(2-methoxycarbonylethyl)-2-{4-[N-(3-cyclohexyloxycarbonylpropyl)amidino]benzoylimino}-3-cyclobutyl-4-methyl-3H-thiazoline-5-carboxamide methylsulfate (Compound 58) was obtained.

m.p. 111°~112° C.

EXAMPLE 50

Following the procedure similar to that of Example 11 using N-(2-methoxycarbonylethyl)-2-[4-(methylthioimidoyl)benzoylimino]-3-cyclopentyl-4-methyl-3H-thiazoline-5-carboxamide methylsulfate obtained in Example 48(4), N-(2-methoxycarbonylethyl)-2-{4-[N-(3-carboxypropyl)amidino]benzoylimino}-3-cyclopentyl-4-methyl-3H-thiazoline-5-carboxamide methylsulfate (Compound 59) was obtained.

m.p. 122°~123° C.

EXAMPLE 51

Following the procedure similar to that of Example 12 using Compound 57, N-(2-carboxyethyl)-2-{4-[N-(3- carboxypropyl)amidino]benzoylimino}-3-cyclopentyl-4-methyl-3H-thiazoline-5-carboxamide (Compound 60) was obtained.

m.p. 102°~103° C.

EXAMPLE 52

Following the procedure similar to that of Example 7 using Compound 58, N-(2-carboxyethyl)-2-{4-[N-(3-cyclohexyloxycarbonylpropyl)amidino]benzoylimino}-3-cyclopentyl-4-methyl-3H-thiazoline-5-carboxamide (Compound 61) was obtained.

m.p. 200°~200.5° C.

EXAMPLE 53

(1) Following the reaction procedure similar to that of Example 34(1) using cyclohexylamine in place of cyclopropylamine, 1-(4-cyanobenzoyl)-3-cyclohexylthiourea was obtained.

m.p. 136°~137° C.

(2) Following the reaction procedure similar to that of Example 34(2) using 1-(4-cyanobenzoyl)-3-cyclohexylthiourea, ethyl 2-(4-cyanobenzoylimino)-3-cyclohexyl-4-methyl-3H-thiazoline-5-carboxylate was obtained.

m.p. 232°~233° C.

(3) A mixture of ethyl 2-(4-cyanobenzoylimino)-3-cyclohexyl-4-methyl-3H-thiazoline-5-carboxylate (39.75 g), 10% aqueous sodium hydroxide solution (44 ml), dimethyl sulfoxide (398 ml) and methylene chloride (199 ml) was stirred at room temperature for an hour, and then the methylene chloride was evaporated under reduced pressure, followed by addition of conc. hydrochloric acid (9.2 ml) and water (500 ml). After separation of the solvent by decantation, and the residue was crystallized with water to give crude 2-(4-cyanobenzoylimino)-3-cyclohexyl-4-methyl-3H-thiazoline-5-carboxylic acid, which was then stirred together with HOBt.H$_2$O (30.63 g), WSC.HCl (21.09 g), triethylamine (15.33 ml) and DMF (500 ml) at room temperature overnight. To the reaction mixture was added water (1 l), and the precipitated crystals were collected by filtration and purified by silica gel column chromatography (methylene chloride—ethyl acetate) to give N-(2-methoxycarbonylethyl)-3-cyclohexyl-2-(4-cyanobenzoylimino)-4-methyl-3H-thiazoline-5-carboxamide (40.7 g).

m.p. 194°~195° C.

(4) Following the procedure similar to that of Example 34(5) using N-(2-methoxycarbonylethyl)-3-cyclohexyl-2-(4-cyanobenzoylimino)-4-methyl-3H-thiazoline-5-carboxamide, N-(2-methoxycarbonylethyl)-2-[4-thiocarbamoylbenzoylimino]-3-cyclohexyl-4-methyl-3H-thiazoline-5-carboxamide was obtained.

m.p. 228°~230° C.

(5) A mixture of N-(2-methoxycarbonylethyl)-2-[4-thiocarbamoylbenzoylimino]-3-cyclohexyl-4-methyl-3H-thiazoline-5-carboxamide (40 g), methyl iodide (100 ml) and acetone (1 l) was stirred under heating reflux for 2 hours. The reaction mixture was concentrated to about 500 ml under reduced pressure, and after cooling to room temperature, the precipitated crystals were collected by filtration to give N-(2-methoxycarbonylethyl)-2-[4-(methylthioimidoyl)benzoylimino]-3-cyclohexyl-4-methyl-3H-thiazoline-5-carboxamide hydroiodide (51.9 g).

m.p. 202.5°~203.5° C. (decomposed)

(6) Following the procedure similar to that of Example 11 using N-(2-methoxycarbonylethyl)-2-[4-(methylthioimidoyl)benzoylimino]-3-cyclohexyl-4-methyl-3H-thiazoline-5-carboxamide hydroiodide and β-alanine, N-(2-methoxycarbonylethyl)-2-{4-[N-(2-carboxyethyl)amidino]benzoylimino}-3-cyclohexyl-4-methyl-3H-thiazoline-5-carboxamide hydroiodide (Compound 62) was obtained.

$^1$H-NMR (DMSO-d$_6$) δ (ppm); 1.3–1.6 (4H, broad), 1.6–2.0 (6H, broad), 2.58 (2H, d, J=6Hz), 2.64 (3H, s), 2.93 (2H, broad), 3.44 (2H, q, J=6Hz), 3.60 (2H, broad), 3.62 (3H, s), 4.30 (1H, broad), 7.90 (2H, d, J=8Hz), 8.30 (2H, d, J=8Hz), 8.40 (1H, t, J=6Hz).

EXAMPLE 54

Following the procedure similar to that of Example 11 using N-(2-methoxycarbonylethyl)-2-[4-(methylthioimidoyl)benzoylimino]-3-cyclohexyl-4-methyl-3H-thiazoline-5-carboxamide hydroiodide obtained in Example 53(5), N-(2-methoxycarbonylethyl)-2-{4-[N-(3-carboxypropyl)amidino]benzoylimino}-3-cyclohexyl-4-methyl-3H-thiazoline-5-carboxamide hydroiodide (Compound 63) was obtained.

m.p. 57°~60° C.

EXAMPLE 55

Following the procedure similar to that of Example 11 using N-(2-methoxycarbonylethyl)-2-[4-(methylthioimidoyl)benzoylimino]-3-cyclohexyl-4-methyl-3H-thiazoline-5-carboxamide hydroiodide obtained in Example 53(5) and 4-aminocaproic acid, N-(2-methoxycarbonylethyl)-2-{4-[N-(4-carboxypentyl)amidino]benzoylimino}-3-cyclohexyl-4-methyl-3H-thiazoline-5-carboxamide hydroiodide (Compound 64) was obtained.

m.p. 77°~79° C.

EXAMPLE 56

A mixture of Compound 62 (0.2 g), 10% aqueous sodium hydroxide solution (0.26 ml) and methanol (2 ml) was stirred at 70° C. for 30 minutes. After evaporation of the solvent, 3% hydrochloric acid was added, and the solvent was separated by decantation, followed by drying to give N-(2-carboxyethyl)-2-{4-[N-(2-carboxyethyl)amidino]benzoylimino}-3-cyclohexyl-4-methyl-3H-thiazoline-5-carboxamide (Compound 65).

m.p. 68°~70° C.

EXAMPLE 57

Following the procedure similar to that of Example 56 using Compound 63, N-(2-carboxyethyl)-2-{4-[N-(3-carboxypropyl)amidino]benzoylimino}-3-cyclohexyl-4-methyl-3H-thiazoline-5-carboxamide (Compound 66) was obtained.

m.p. 183°~186° C.

EXAMPLE 58

Following the procedure similar to that of Example 56 using Compound 64, N-(2-carboxyethyl)-2-{4 -[N-(4-carboxypentyl)amidino]benzoylimino}-3-cyclohexyl-4-methyl-3H-thiazoline-5-carboxamide (Compound 67) was obtained.

$^1$H-NMR (DMSO-d$_6$) δ (ppm); 1.3–2.0 (14H, broad), 2.25 (2H, t, J=6Hz), 2.50 (2H, t, J=6Hz), 2.63 (3H, s), 2.94

(2H, broad), 3.42 (4H, broad), 4.31 (1H, broad), 7.91 (2H, d, 8Hz), 8.31 (2H, d, 8Hz), 8.36 (1H, t, 6Hz), 9.20 (1H, broad), 9.55 (1H, broad), 9.88 (1H, t, 6Hz).

We claim:

1. A thiazoline derivative represented by the formula:

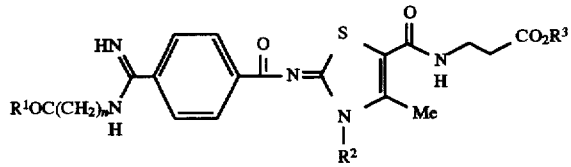

wherein $R^1$ is a hydroxyl group, an alkoxy group having 1 to 6 carbon atoms, a cycloalkoxy group having 3 to 6 carbon atoms or a group represented by the formula:

$R^4NH-$ wherein $R^4$ is a cycloalkyl group having 3 to 6 carbon atoms or a phenyl group, $R^2$ is an alkyl group having 1 to 14 carbon atoms, a cycloalkyl group having 3 to 6 carbon atoms or a phenylalkyl group having 7 to 10 carbon atoms, $R^3$ is a hydrogen atom or an alkyl group having 1 to 6 carbon atoms, and n is an integer of 2 to 9 or a pharmaceutically acceptable salt thereof.

2. The thiazoline derivative or the pharmaceutically acceptable salt thereof according to claim 1, wherein $R^3$ is a hydrogen atom.

3. The thiazoline derivative or the pharmaceutically acceptable salt thereof according to claim 1, wherein $R^3$ is a hydrogen atom and $R^1$ is a hydroxyl group.

4. The thiazoline derivative or the pharmaceutically acceptable salt thereof according to claim 1, wherein $R^1$ is a hydroxyl group, $R^3$ is a hydrogen atom and $R^2$ is a methyl group.

5. The thiazoline derivative or the pharmaceutically acceptable salt thereof according to claim 1, which is selected from the group consisting of N-(2-carboxyethyl)-2-{4-[N-(3-carboxypropyl)amidino]benzoylimino}-3,4-dimethyl-3H-thiazoline-5-carboxamide and N-(2-carboxyethyl)-2-{4-[N-(2-carboxyethyl)amidino]benzoylimino}-3,4-dimethyl-3H-thiazoline-5-carboxamide.

* * * * *